(12) United States Patent
Gao et al.

(10) Patent No.: US 11,345,689 B2
(45) Date of Patent: May 31, 2022

(54) COMPOUND AND ORGANIC LIGHT EMITTING DISPLAY DEVICE

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Xiangcheng Wang, Shanghai (CN); Lei Zhang, Shanghai (CN); Jinghua Niu, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 590 days.

(21) Appl. No.: 16/052,631

(22) Filed: Aug. 2, 2018

(65) Prior Publication Data

US 2018/0370957 A1 Dec. 27, 2018

(30) Foreign Application Priority Data

May 3, 2018 (CN) .......................... 201810415384.1

(51) Int. Cl.
*C07D 409/04* (2006.01)
*C07D 409/14* (2006.01)
*C07D 409/10* (2006.01)
*C07D 333/36* (2006.01)
(Continued)

(52) U.S. Cl.
CPC ......... *C07D 409/04* (2013.01); *C07D 333/36* (2013.01); *C07D 409/10* (2013.01);
(Continued)

(58) Field of Classification Search
None
See application file for complete search history.

(56) References Cited

U.S. PATENT DOCUMENTS

2004/0110031 A1 6/2004 Fukuda et al.
2006/0087224 A1* 4/2006 Oki .................... H01L 51/5243
313/504
(Continued)

FOREIGN PATENT DOCUMENTS

CN 1466583 A 1/2004
CN 103247761 A 8/2013
(Continued)

OTHER PUBLICATIONS

Machine English translation of Li et al. (CN 106220649 A). Jan. 23, 2021.*
Ikemoto et al. (Heterocycles 1997, 46, p. 489).*

Primary Examiner — Jay Yang
(74) Attorney, Agent, or Firm — Kilpatrick Townsend & Stockton, LLP

(57) ABSTRACT

The disclosure relates to the technical field of organic electroluminescent materials, and particularly to a compound and an organic light emitting display device. The compound has structure shown as formula (I):

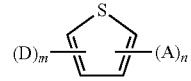

Formula (I)

where D represents an electron donor unit, A represents an electron acceptor unit, in and n are each independently selected from 1, 2 or 3, and m+n≤4. When the compound of the present disclosure is used as a light emitting material, a guest material, or a host material of an organic light emitting display device, higher light emitting efficiency can be achieved.

22 Claims, 1 Drawing Sheet

(51) Int. Cl.
*H01L 51/00* (2006.01)
*H01L 51/50* (2006.01)

(52) U.S. Cl.
CPC .......... *C07D 409/14* (2013.01); *H01L 51/008* (2013.01); *H01L 51/0061* (2013.01); *H01L 51/0067* (2013.01); *H01L 51/0068* (2013.01); *H01L 51/0072* (2013.01); *H01L 51/5024* (2013.01); *H01L 51/5004* (2013.01); *H01L 51/5012* (2013.01); *H01L 51/5016* (2013.01); *H01L 2251/552* (2013.01)

(56) References Cited

U.S. PATENT DOCUMENTS

2009/0072727 A1\* 3/2009 Takeda ................... C09K 11/06
 313/504
2015/0129849 A1\* 5/2015 Kwong ............... H01L 51/0059
 257/40

FOREIGN PATENT DOCUMENTS

| CN | 104177344 A | | 12/2014 |
|---|---|---|---|
| CN | 105810846 A | | 7/2016 |
| CN | 106220649 A | \* | 12/2016 |
| CN | 107698601 A | | 2/2018 |
| CN | 108358905 A | | 8/2018 |
| CN | 108864068 A | | 11/2018 |
| CN | 108997400 A | | 12/2018 |
| JP | 2004-171808 A | | 6/2004 |
| WO | 2014/204464 A1 | | 12/2014 |
| WO | WO-2016/046310 A1 | \* | 3/2016 |

\* cited by examiner

COMPOUND AND ORGANIC LIGHT EMITTING DISPLAY DEVICE

CROSS-REFERENCE OF RELATED APPLICATION

The present application claims priority to Chinese Patent Application No. 201810415384.1 and filed with the Chinese Patent Office on May 3, 2018, the content of which is hereby incorporated by reference in its entirely.

FIELD

The disclosure relates to the technical field of organic electroluminescent materials, and particularly to a compound and an organic light emitting display device.

BACKGROUND

According to the light emitting mechanism, there are mainly four kinds of materials that can be used for the light emitting layers of OLEDs: fluorescent materials, phosphorescent materials, triplet-triplet annihilation (TTA) materials and thermally activated delayed fluorescence (TADF) materials. The theoretical maximum internal quantum yield of the fluorescent materials does not exceed 25%, the theoretical maximum internal quantum yield of the TTA materials does not exceed 62.5%, and the theoretical maximum internal quantum yields of the phosphorescent materials and the TADF materials are both up to 100%. However, the phosphorescent materials basically refer to heavy metal complexes such as Ir. Pt, Os, Re, and Ru, which have high production cost and therefore are not conducive to large-scale production. Besides, at a high current density, the phosphorescent materials are subject to severe efficiency roll-off. In addition, the stability of phosphorescent devices is poor.

The TADF materials are mainly organic compounds, do not require rare metal elements, have low production costs, and can be chemically modified by various methods.

SUMMARY

The present disclosure provides a compound and an organic light emitting display device.

One embodiment of the present disclosure provides a compound having a structure shown as a formula (I):

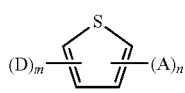

Formula (I)

Wherein D represents an electron donor unit, A represents an electron acceptor unit, in and n are each independently selected from 1, 2 or 3, and m+n≤4.

According to one embodiment of the present disclosure, in the compound, at least one D unit and at least one A unit are respectively linked to an adjacent —CH— on a

ring.

Another embodiment of the present disclosure further provides an organic light emitting display device, including an organic electroluminescent device, and the organic electroluminescent device includes: an organic functional layer including one or more organic film layers, and at least one of the organic film layers is a light emitting layer; the light emitting layer includes a light emitting material, and the light emitting material includes any one or more of the above compounds.

According to one embodiment of the present disclosure, the compound functions as a host material or a dopant material of the light emitting layer, or the compound constitutes the light emitting layer alone to prepare a non-doping organic light emitting display device.

According to one embodiment of the disclosure, the light emitting material is a thermally activated delayed fluorescence material.

BRIEF DESCRIPTION OF THE DRAWINGS

FIG. 1(A) shows the HOMO energy level distribution of compound P1, and FIG. 1(B) shows the LUMO energy level distribution of compound P1;

DETAILED DESCRIPTION

Figure 1:
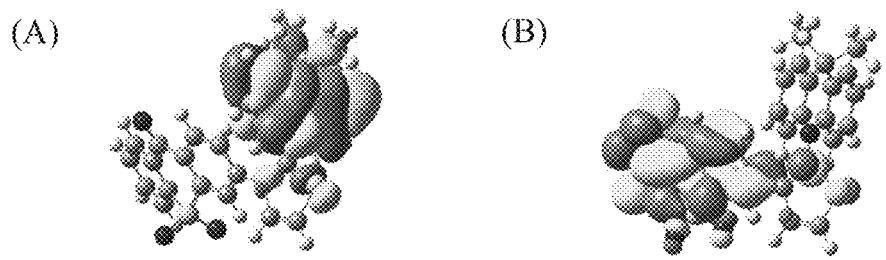
FIG. 1 is a graph showing the distribution of HOMO and LUMO energy levels of compound P1.

The embodiments are merely illustrations of the present disclosure, but not considered as limiting the content of the present disclosure. The present disclosure will be further explained and described below in conjunction with embodiments.

The present disclosure provides a compound and an organic light emitting display ilk device.

One embodiment of the present disclosure provides a compound having a structure shown as the formula (I):

Formula (I)

where D represents an electron donor unit, A represents an electron acceptor unit, m and n are each independently selected from 1, 2 or 3, and m+n≤4.

The compound according to the present disclosure can be used as a thermally activated delayed fluorescence (TADF) material. When the value of the energy gap between $S_1$ state and $T_1$ state is small and the lifetime of a $T_1$-state exciton is long, under certain temperature conditions, the $T_1$-state exciton can realize the process of $T_1 \rightarrow S_1$ through reverse inter-system crossing (RISC) and then is radiatively attenuated to a ground state $S_0$ from $S_1$ state.

The compound according to the present disclosure reduces the overlapping degree of HOMO and LUMO by introducing the electron donor unit D and the electron acceptor unit A and a building unit with large steric hindrance. Since ΔEst is positively correlated with the overlapping degree of HOMO and LUMO, the energy level difference ΔEst between $S_1$ state and $T_1$ state of the compound of the present disclosure is small.

When the compound of the present disclosure is used as a light emitting material, a guest material, or a host material of an organic light emitting display device, due to the introduction of the thiophene group, the interaction between the D unit and the A unit in the molecule becomes stronger, the molecular twisting strength increases, and a larger dihedral angle is formed; therefore, effective separation of the HOMO orbit from the LUMO is achieved, the exciton quenching caused by π-π stacking is weakened, and moreover, the molecule maintains a certain degree of molecular rigidity so that a higher photoluminescence quantum yield (PLQY) can be achieved, thereby obtaining a more satisfactory device performance.

The present disclosure employs the thiophene group as bridging moieties and has the following advantages.

1) The chemical modification method based on a thiophene unit has been very mature. The different sites of the thiophene unit can be functionally modified by a variety of methods effectively, so that the physical and chemical properties of the materials are regulated in a wide range.

2) Thiophene materials have excellent chemical and physical properties.

3) Due to their good stability, unique electrical, optical, redox and self-assembly properties, thiophene materials become important candidates for organic electronics materials.

4) Because the sulfur atom on the thiophene ring has excellent polarizability and high electron-richness, the thiophene organic materials have excellent charge transport performance and electron donation performance.

The D-A molecular structure facilitates the efficient separation of HOMO and LUMO.

According to one embodiment of the present disclosure, in the compound, at least one D unit and at least one A unit are respectively linked to an adjacent —CH— on the

ring.

When at least one D unit and at least one A unit are respectively linked to an adjacent —CH— on the

ring, the following advantages are achieved.

Firstly, the D unit and the A unit are linked by the ortho-position of the thiophene ring therebetween to increase the dihedral angle between the D unit and the A unit, resulting in large steric hindrance between the D unit and the A unit, thereby obtaining a smaller $ΔE_{st}$. Secondly, the ortho-position linking increases the intramolecular space limitation, which can reduce the positive solvatochromism effect of the molecule, and also can improve the luminescent color purity of the molecule and achieve a lower peak width at half height.

The D unit according to the present disclosure should have excellent electron donating property, a higher triplet energy level, a suitable HOMO energy level, and good hole transport performance.

According to one embodiment of the present disclosure, the D unit is any one or more of the following structures:

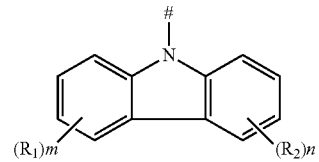

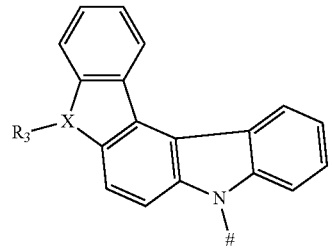

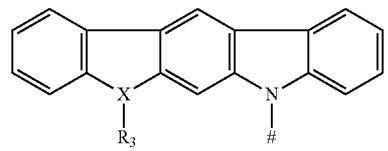

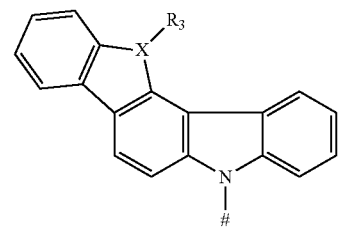

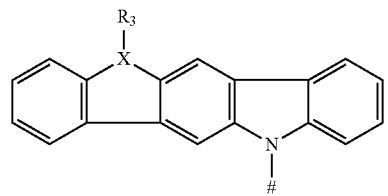

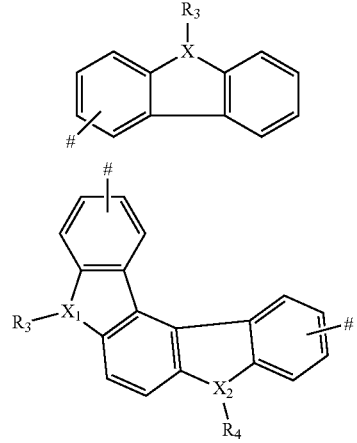

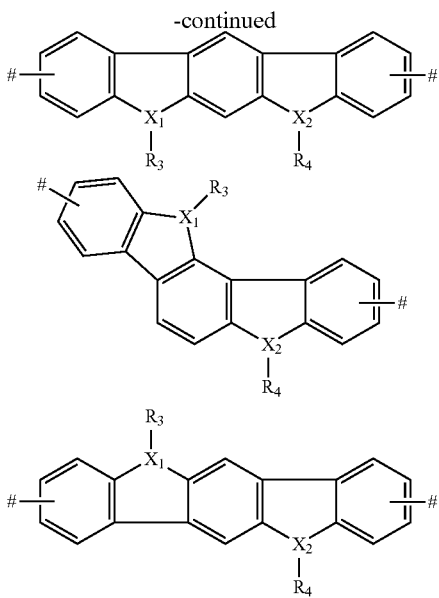

where X, X₁ and X₂ are each independently selected from a carbon atom, a nitrogen atom, an oxygen atom, a sulfur atom or a silicon atom;

# represents a position which can be linked to

m and n are each independently selected from 0, 1, 2 or 3;

R₁, R₂, R₃, and R₄ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups.

When X is an oxygen atom or a sulfur atom, R₃ is not present; when X₁ is an oxygen atom or a sulfur atom, R₃ is not present; when X₂ is an oxygen atom or a sulfur atom, R₄ is not present.

The alkyl group having 1 to 20 carbon atoms may be selected from, for example, one or more of saturated aliphatic hydrocarbon groups such as methyl, ethyl, n-propyl, isopropyl, n-butyl, sec-butyl, or tert-butyl, and the like.

The alkoxy group having 1 to 20 carbon atoms may be selected from, for example, one or more of aliphatic alkoxy groups such as methoxy, ethoxy, propoxy, and the like.

The aryl group having 6 to 40 carbon atoms may be selected from, for example, one or more of aromatic hydrocarbyl groups such as phenyl, biphenylyl, 9,9-fluorenyl, and phenyltriterphenyl, and the like. The aryl group having 6 to 40 carbon atoms may have substituents or may not have substituents.

The heteroaryl group having 4 to 40 carbon atoms may be selected from, for example, furyl, pyrrolyl, pyridyl, thiazolyl, pyrazinyl, imidazolyl, pyrazolyl, pyrimidinyl thienyl, and the like. The heteroaryl group having 4 to 40 carbon atoms may have substituents or may not have substituents.

For the above terms mentioned elsewhere in this article, the same understanding as above should also be made.

In the present disclosure, the "substituted or unsubstituted carbazolyl group having 12 to 40 carbon atoms and its derivative groups" means that the carbazolyl group and its derivative groups may be substituted or unsubstituted, and the total number of carbon atoms in the carbazolyl group and its derivative groups (including the substituent, if present) is 12-40. The derivative groups refer to compounds in which hydrogen atom or atomic group in a carbazolyl group is substituted by other atoms or atom groups.

For the "substituted or unsubstituted diphenylamino group having 12 to 40 carbon atoms and its derivative groups", the "substituted or unsubstituted acridinyl group having 12 to 40 carbon atoms and its derivative groups", the "substituted or unsubstituted azine group having 3 to 40 carbon atoms and its derivative groups", they should also be construed similarly.

In one embodiment, the D unit is selected from any one or more of the following structures:

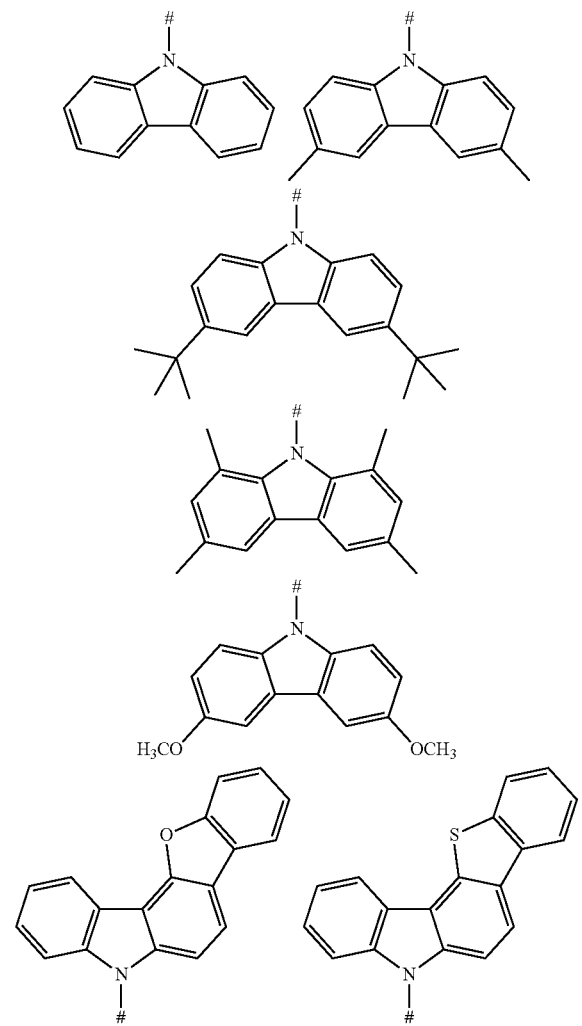

-continued
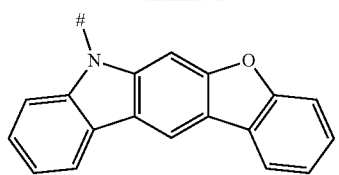
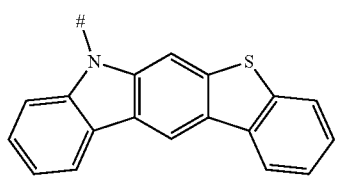
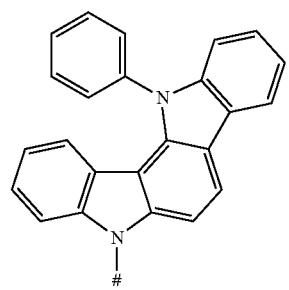
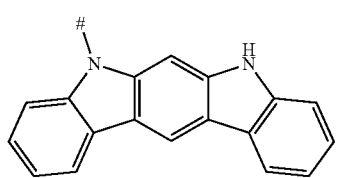
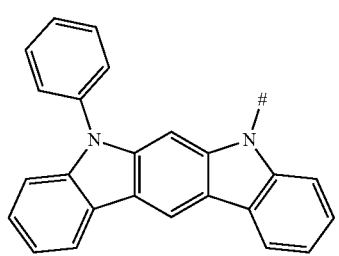
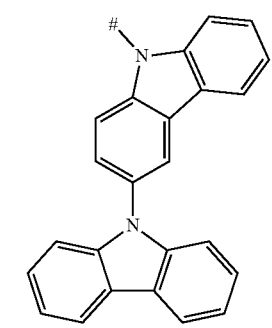
-continued
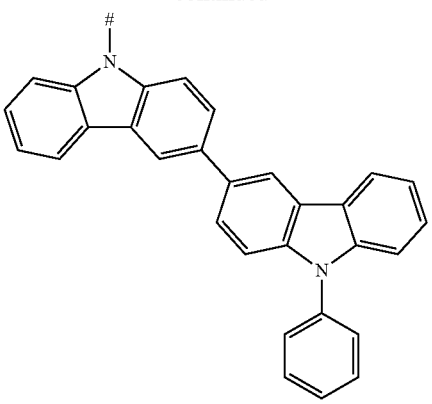
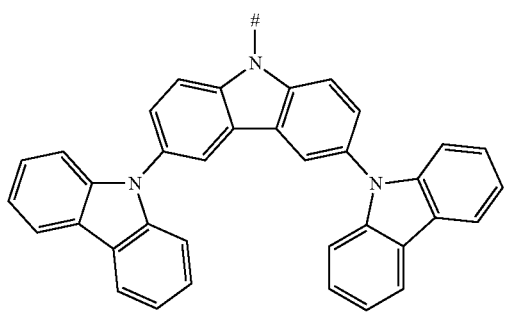
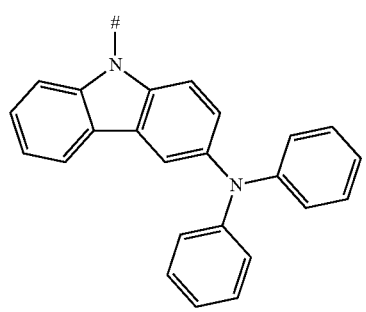
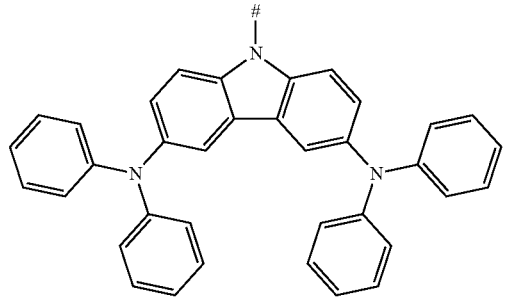
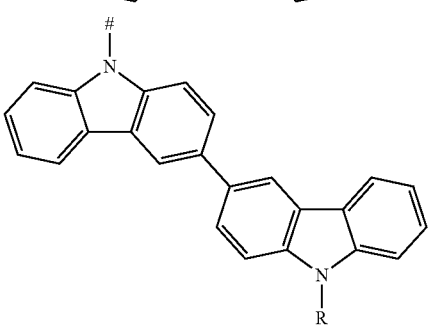

-continued where, # represents a position which is linked to

[thiophene structure],

R in each structural formula independently represents an alkyl group having 1 to 20 carbon atoms, an alkoxy group having 1 to 20 carbon atoms, an alkenyl group having 2 to 20 carbon atoms, an alkynyl group having 2 to 20 carbon atoms, an aromatic group having 6 to 40 carbon atoms, and a heteromatic group having 4 to 40 carbon atoms.

When D unit is selected from the above carbazolyl group and its derivative groups, it has the following advantages: 1. the raw material is cheap and the cost is low; 2. the modification of molecular properties is easily performed without changing the main skeleton structure of the molecule; 3. the N atoms are easily modified functionally; 4. the carbazole group has multiple linking positions to be linked with other molecular structures; 5. the thermal stability and chemical stability are good; 6. the triplet energy level is high; and 7. excellent electron donating property and luminescent property and good hole transport property are achieved.

This type of target compounds may be selected from the following:

P4

P5

P6

P9

P17

-continued

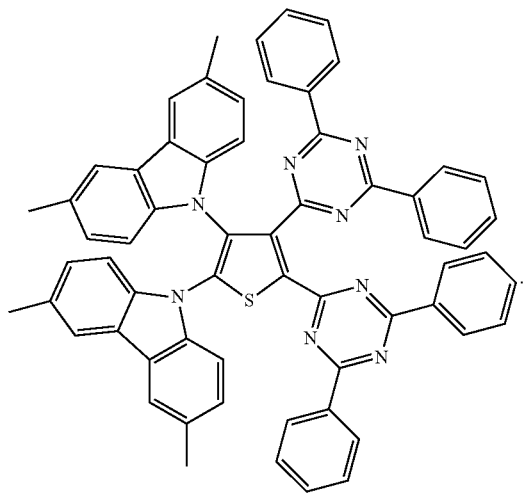

P30

According to one embodiment of the present disclosure, the D unit is selected from any one or more of the following structures:

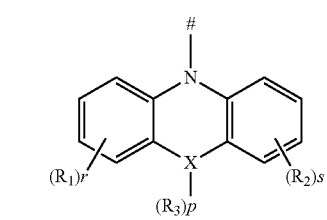

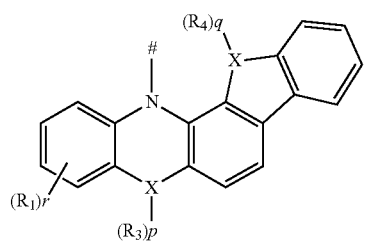

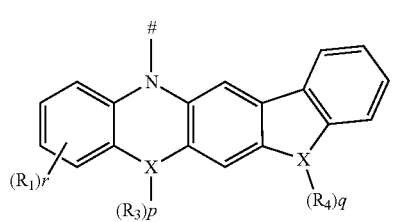

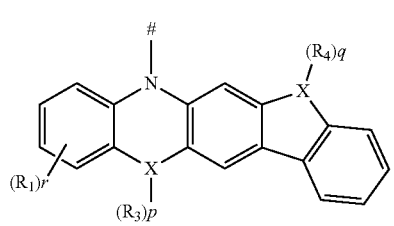

-continued

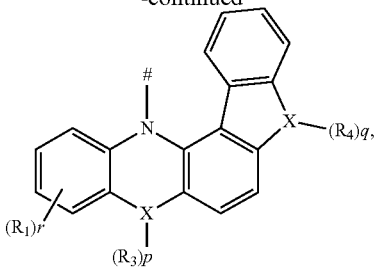

where X is selected from a carbon atom, a nitrogen atom, an oxygen atom, a sulfur atom or a silicon atom;
# indicates a position which is linked to

;

r and s are each independently selected from 0, 1, 2 or 3; p and q are each independently selected from 0, 1 or 2;

$R_1$, $R_2$, $R_3$, and $R_4$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups.

When X represents an oxygen atom or a sulfur atom, p=0 and q=0; when X represents a nitrogen atom, p and q are each independently selected from 0 or 1; when X represents a carbon atom or a silicon atom, p and q are each independently selected from 0, 1 or 2.

In one embodiment, the D unit is selected from any one or more of the following structures:

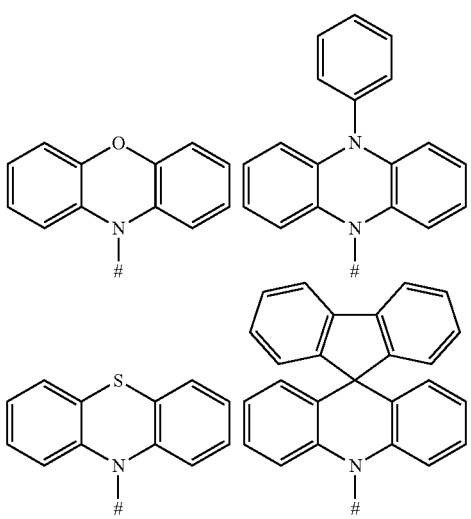

-continued

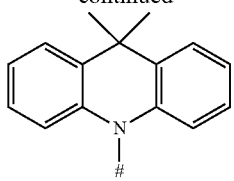

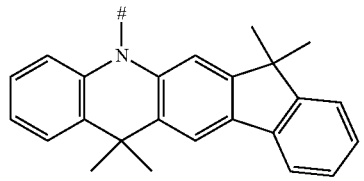

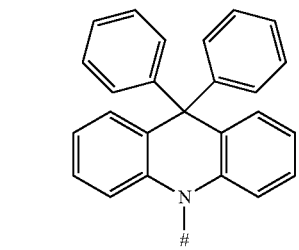

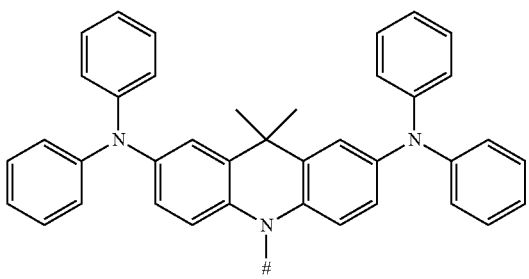

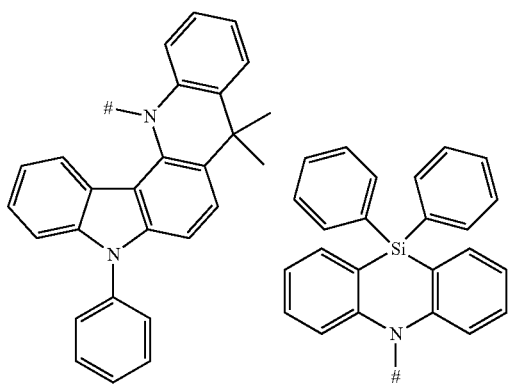

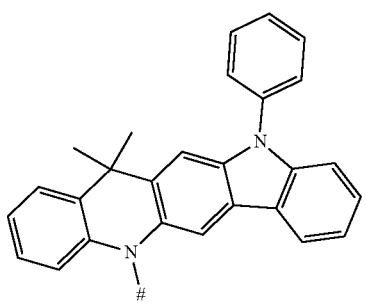

-continued

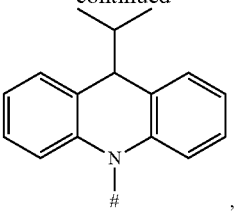

where # indicates a position which is linked to

When the D unit is selected from the above acridinyl group and its derivative groups, it has the following advantages: 1. very strong electron donating property and shorter delay fluorescence lifetime are achieved; 2. better separation of HOMO and LUMO is realized; 3. the rigid molecular structure can effectively reduce the non-radiative attenuation of the excited state 4. the rigid molecular structure reduces the free rotational vibration in the molecule, which is beneficial to the increase of the monochromaticity of the material, and the decrease of the FWHM (full width at half maximum) of the material; and 5. high triplet energy level is achieved.

This type of target compounds may be selected from the following:

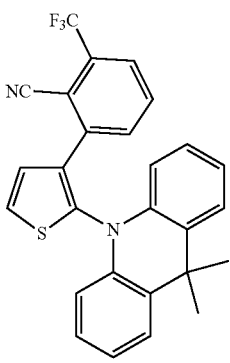

P1

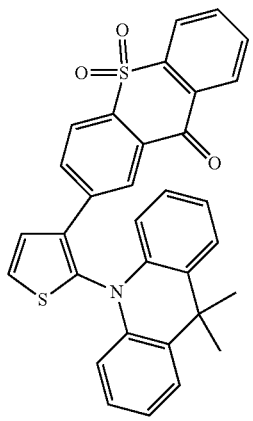

P2

P3

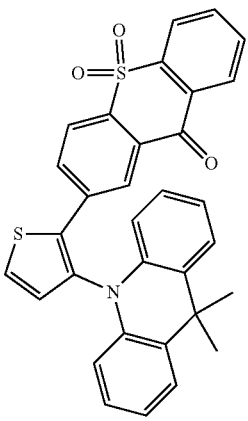

P11

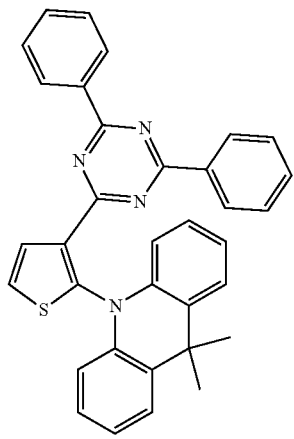

P14

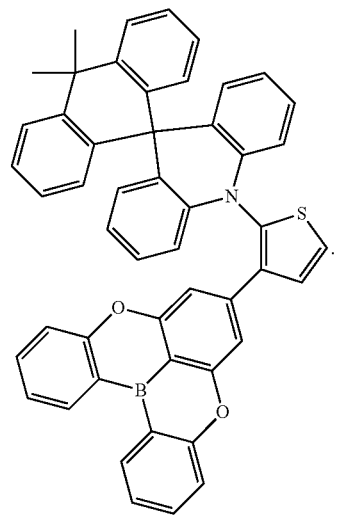

According to one embodiment of the present disclosure, the D unit is selected from any one or more of the following structures:

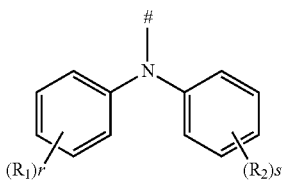

where # indicates a position which is linked to

r and s are each independently selected from 0, 1, 2 or 3;

$R_1$ and $R_2$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups.

In one embodiment, the D unit is selected from any one or more of the following structures:

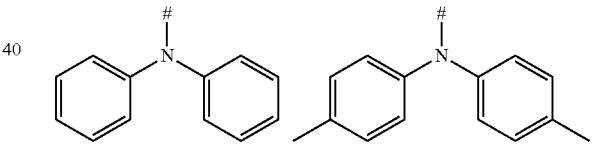

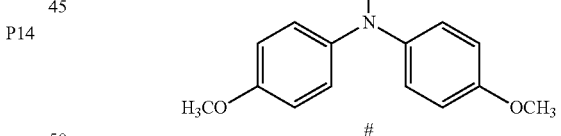

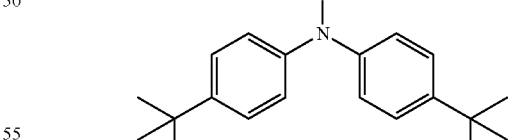

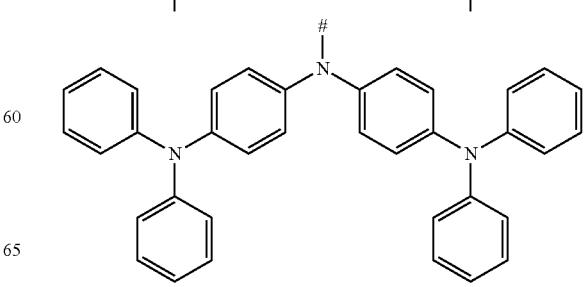

-continued

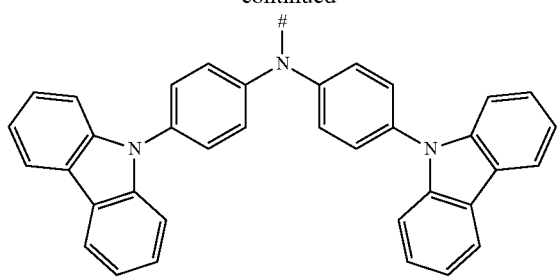

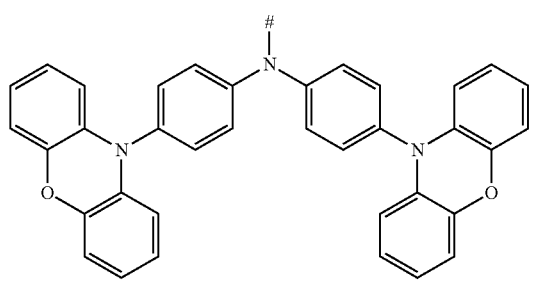

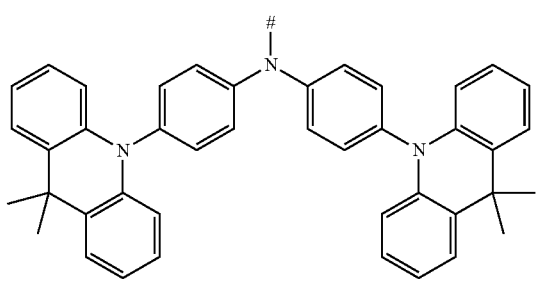

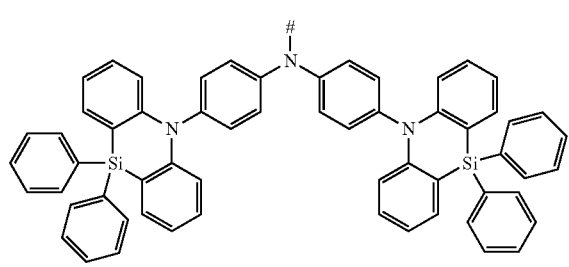

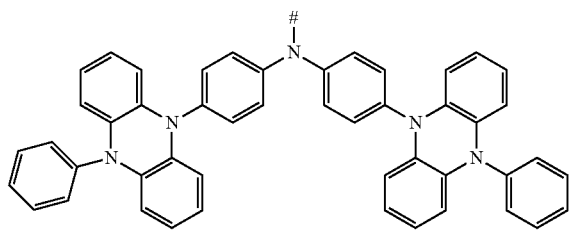

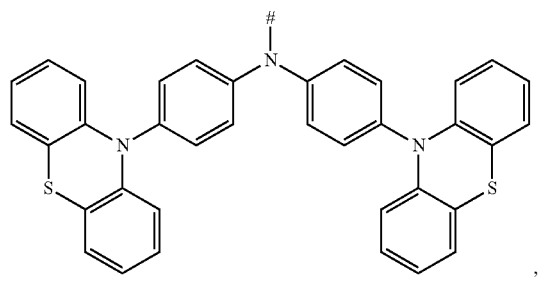

, where # indicates a position which is linked to

When the D unit is selected from the above diphenylamino group and its derivative groups, it has the following advantages: 1. moderate electron donating property is achieved; and 2. good thermal stability and chemical stability are achieved, the source of raw materials is wide, the cost is low, chemical modification is easily performed, and spatial separation of HOMO and LUMO can be effectively achieved when the D unit is combined with the electron acceptor.

This type of target compound may be selected from the following:

P10

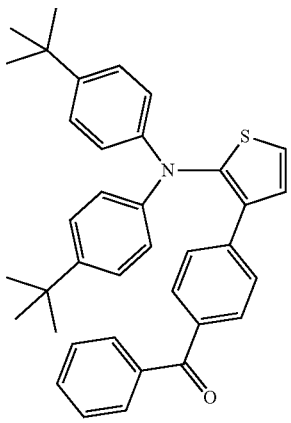

P28

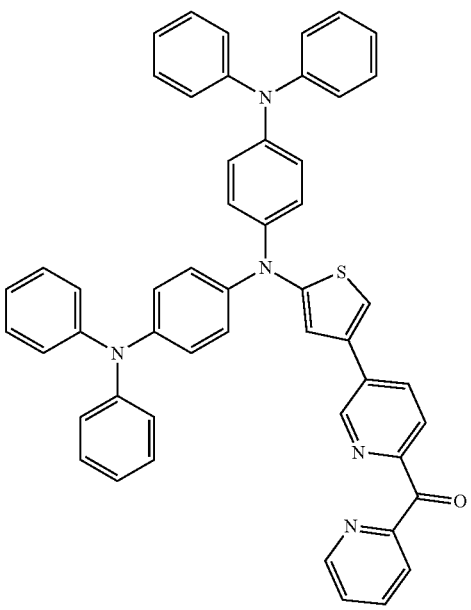

-continued

P18

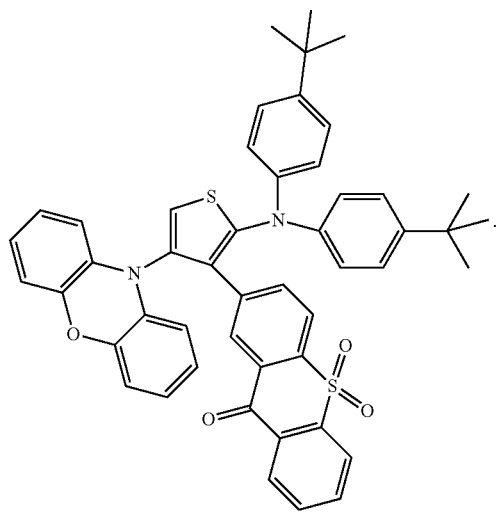

According to one embodiment of the present disclosure, the D unit is selected from any one or more of the following structures:

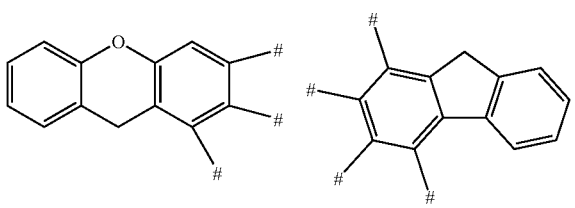

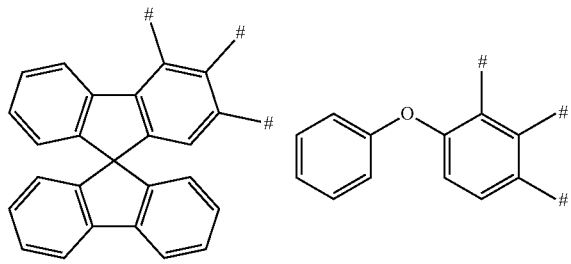

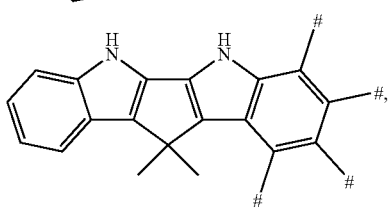

where # indicates a position which can be linked to

According to one embodiment of the present disclosure, the A unit is selected from one or more of nitrogen-containing heterocyclic substituent, cyano substituent, tri-aryl boron substituent, benzophenone substituent, aromatic heterocyclic ketone substituent, and sulfone substituent.

The cyano substituent has strong electron-withdrawing property, can effectively suppress non-radiative transitions, and can construct D-A TADF molecules with low ΔEST and high radiative transition rate constant kr.

Since the boron atom has an empty p orbital, when the boron atom is linked to an aromatic ring, a conjugate plane can be provided, and the substituents on the aromatic ring can also protect the boron atom from being damaged by oxygen and water, so that the entire molecule has better optical property and thus can be used to synthesize a triaryl derivative, and the resulting triaryl boron substituent can be used to construct D-A TADF materials.

The benzophenone substituent contains an electron-deficient carbonyl group (C=O), and has a large torsion angle between the carbonyl group and the benzene ring when serving as an electron acceptor; thus the benzophenone substituent is a pure organic phosphor having very efficient intersystem crossing (kISC=$10^{11}$ $s^{-1}$) and is very suitable for use as an electron acceptor to construct a D-A TADF blue light molecule.

When the sulfone substituent is used as electron acceptor, it has good electron-withdrawing property, shows a certain torsion angle at the center of a molecule to obtain a lower ΔEST value and thus can be used as an electron acceptor to construct a D-A TADF molecule.

The nitrogen-containing heterocyclic substituent is selected from any one or more of the following structures:

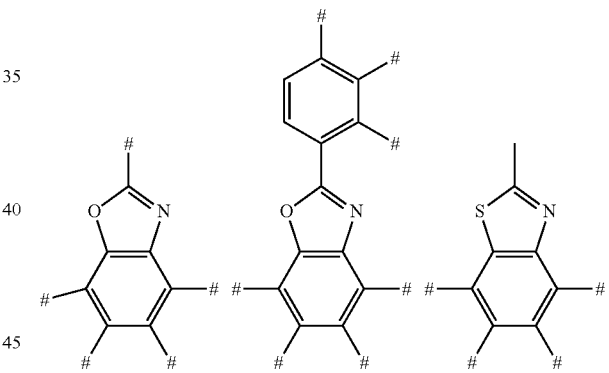

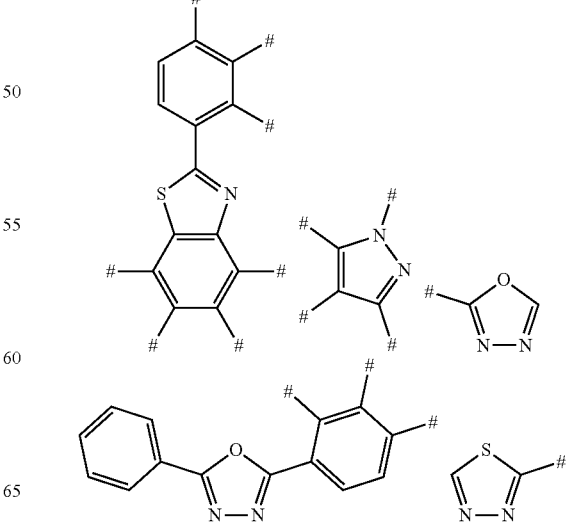

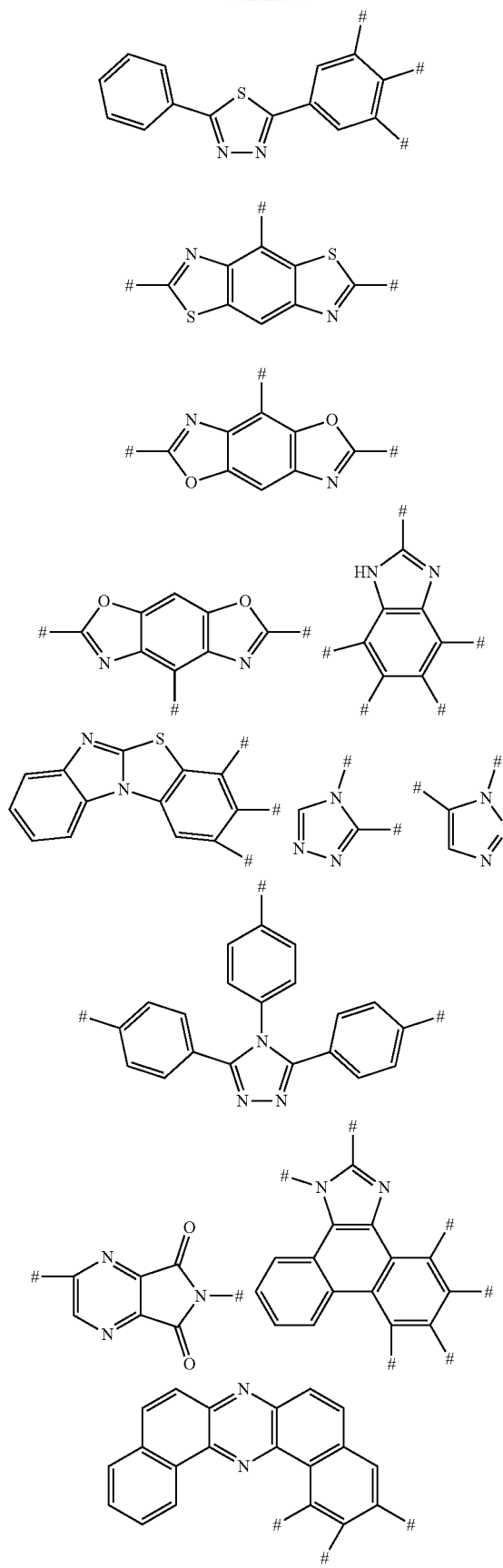
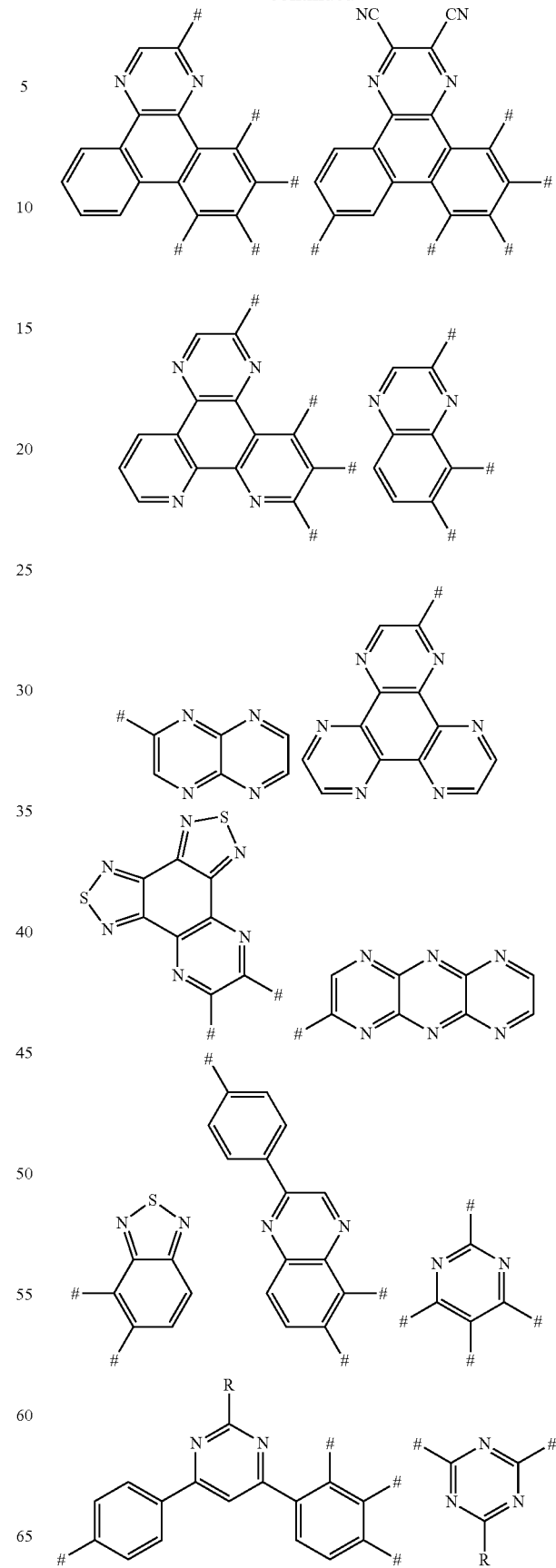

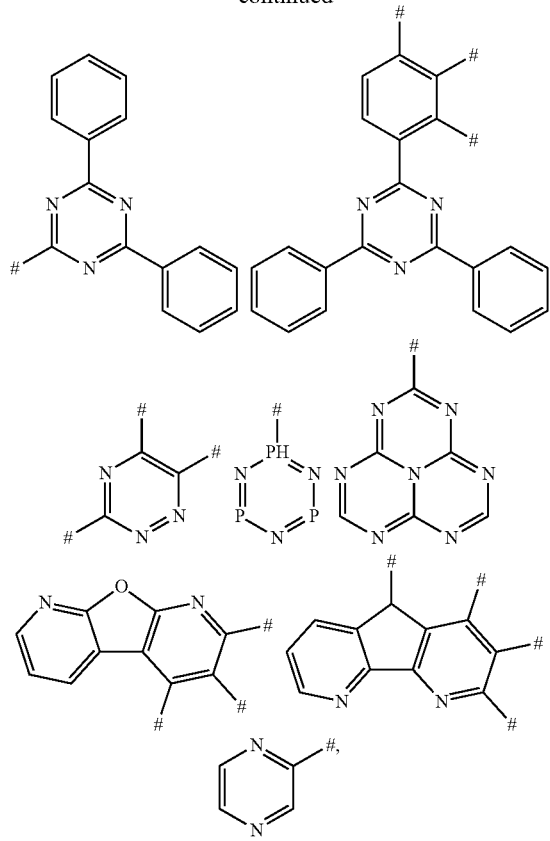

where # indicates a position which can be linked to

R is selected from a hydrogen atom an alkyl group having 1 to 20 carbon atoms, an alkoxy group having 1 to 20 carbon atoms, a cycloalkyl group having 4 to 8 carbon atoms, and an aryl group having 4 to 20 carbon atoms and a heteroaryl group having 4 to 20 carbon atoms.

The target compounds with the nitrogen-containing heterocyclic substituent as an electron acceptor may be selected from:

P22

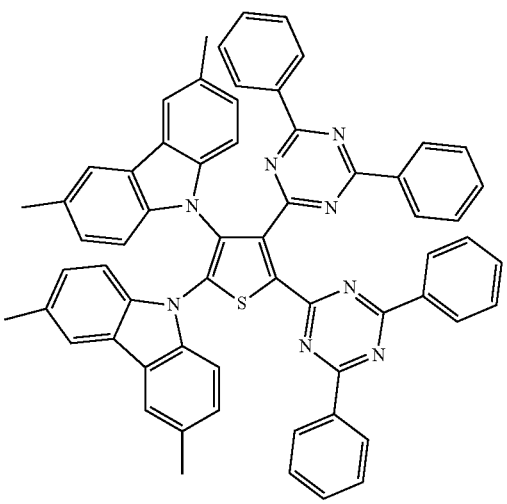

P30

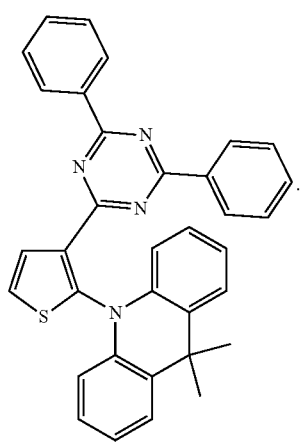

P11

The cyano substituent is selected from one or more of the following structures:

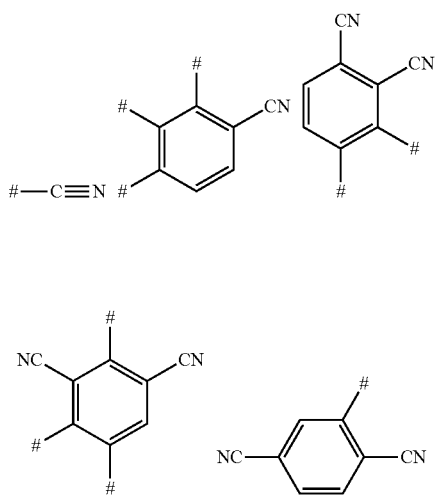

-continued
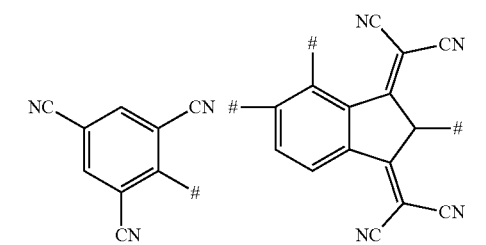
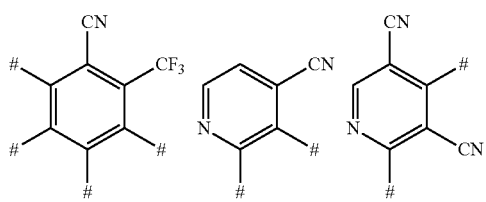
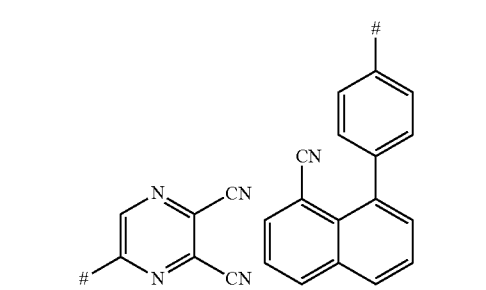
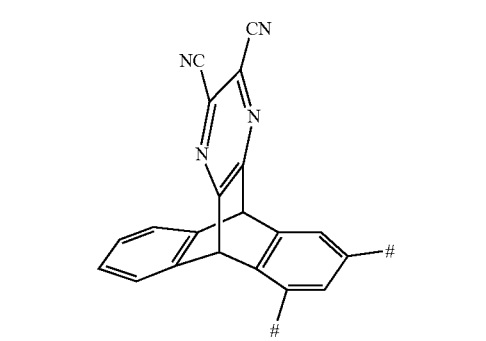
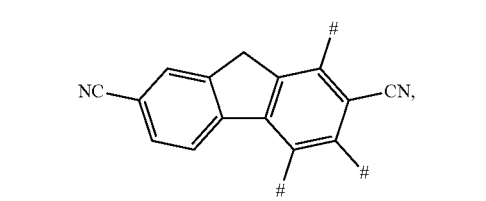
where # indicates a position which can be linked to
The target compounds with the cyano substituent as an electron acceptor may be selected from:
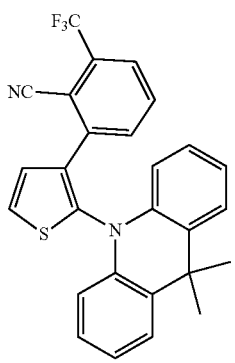
P1
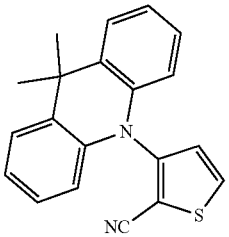
P13
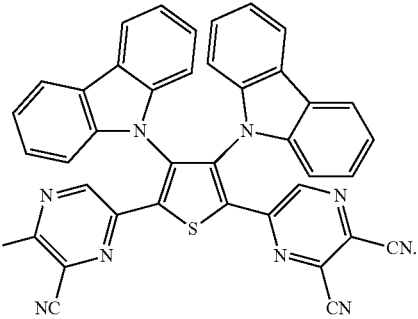
P19
The aryl boron substituent is selected from one or more of the following structures:
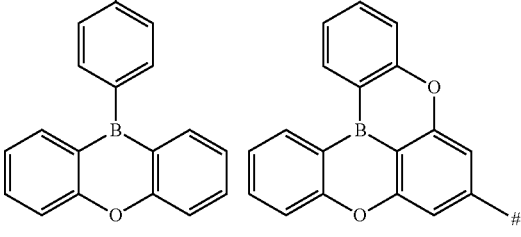
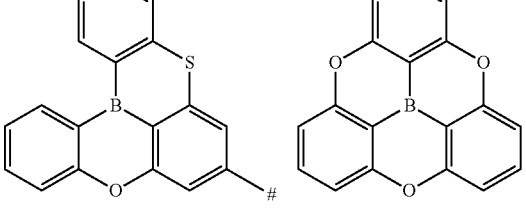

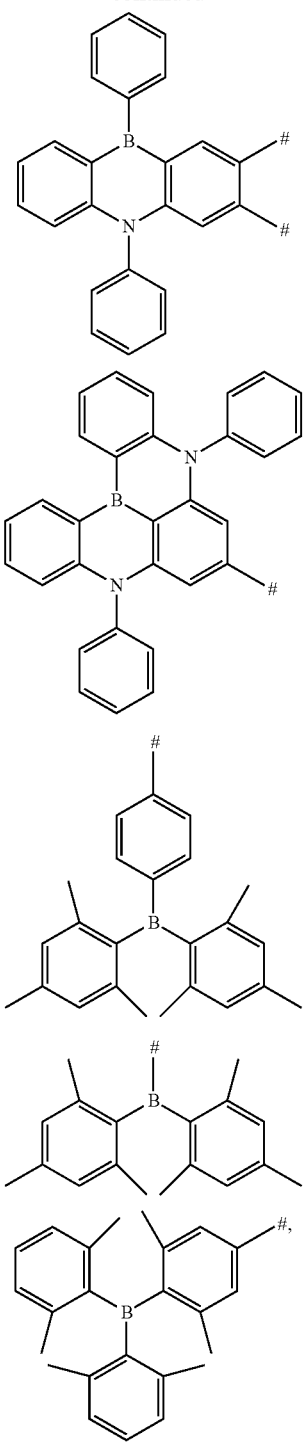
where # indicates a position which can be linked to
The target compounds with the aryl boron substituent as an electron acceptor may be selected from:
P5
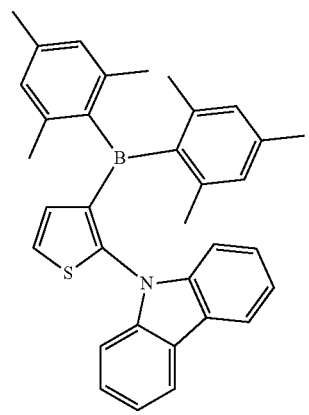
P6
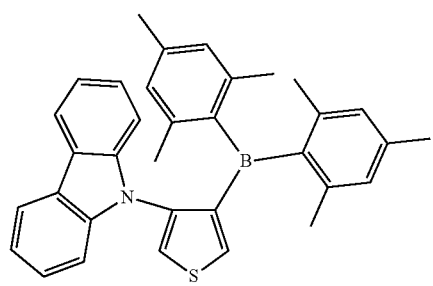
P8
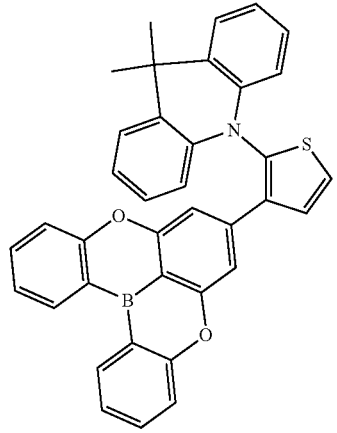
P14
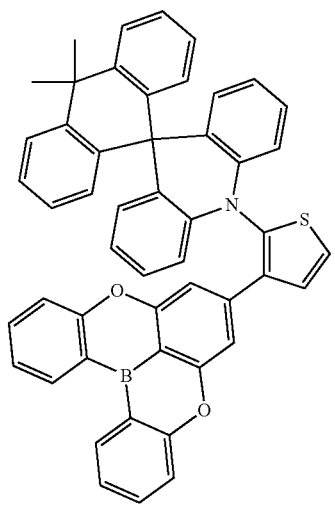

-continued

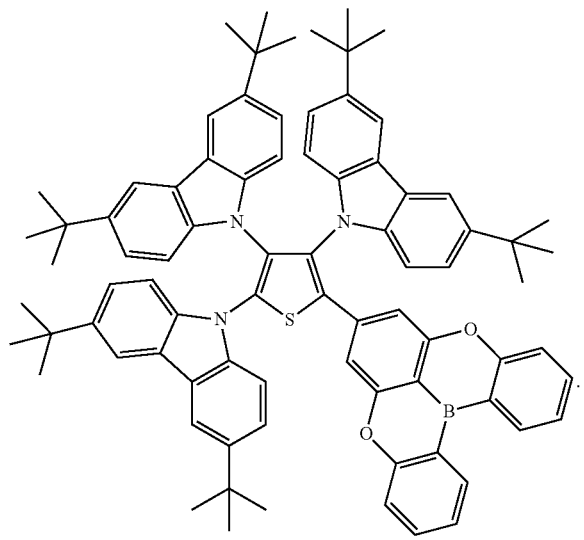

P23

The aromatic ketone substituent or the aromatic heterocyclic ketone substituent is selected from one or more of the following structures:

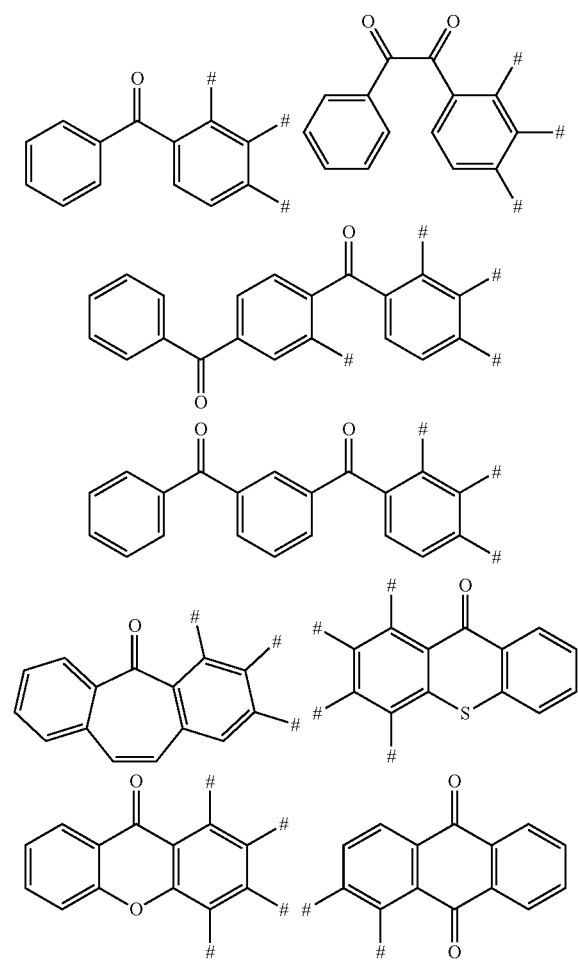

-continued

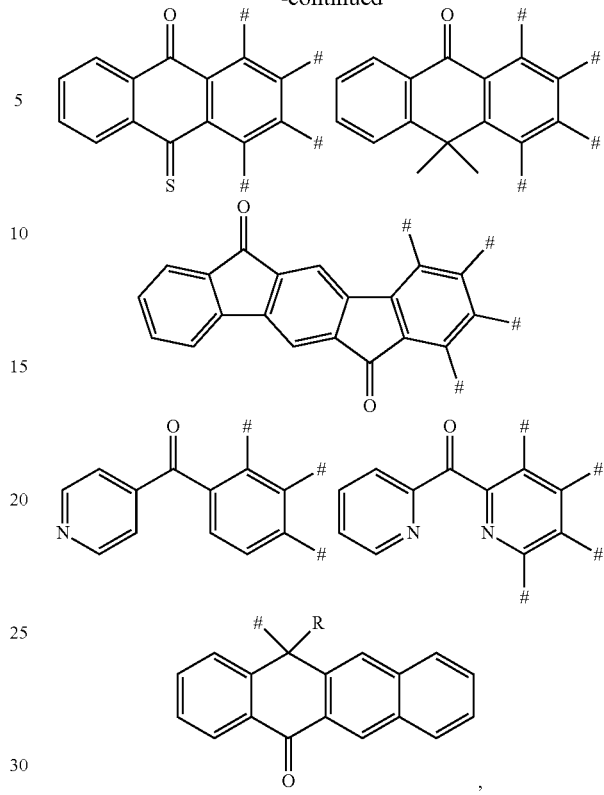

where # represents a position which can be linked to

R in each structural formula independently represents an alkyl group having 1 to 20 carbon atoms, an alkoxy group having 1 to 20 carbon atoms, an alkenyl group having 2 to 20 carbon atoms, an alkynyl group having 2 to 20 carbon atoms, a naphthenic group having 4 to 8 carbon atoms, an aromatic group having 6 to 40 carbon atoms, or a heteromatic group having 4 to 40 carbon atoms.

The target compounds with the aromatic ketone substituent or the aromatic heterocyclic ketone substituent as an electron acceptor may be selected from:

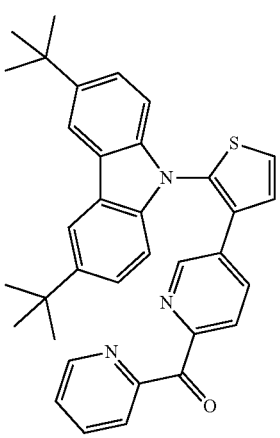

P9

-continued
P10
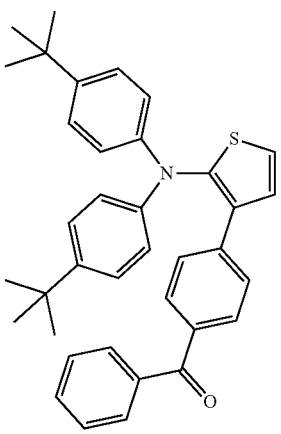
P28
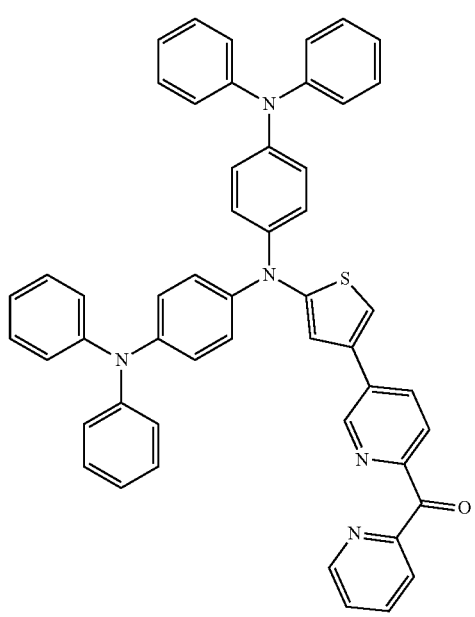
P29
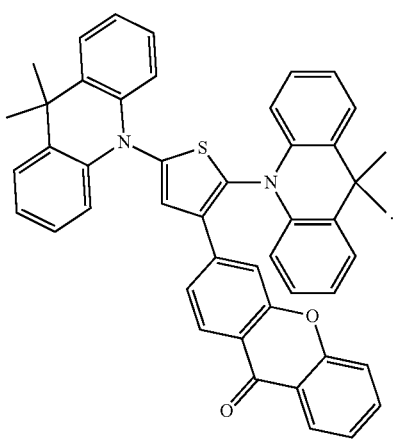
The sulfone substituent is selected from one or more of the following structures:
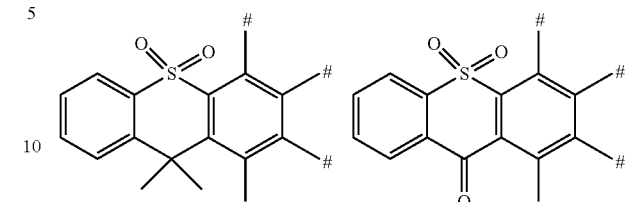
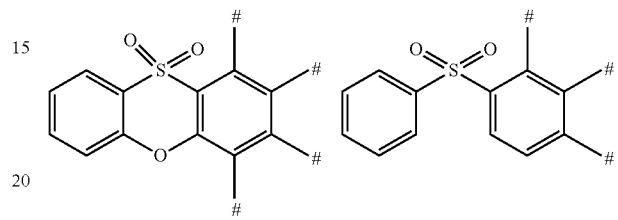
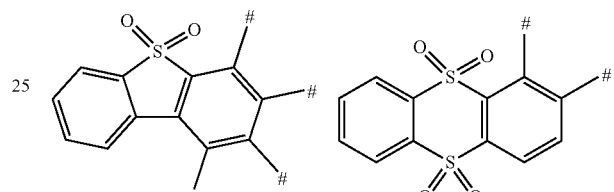
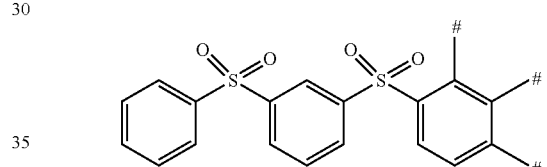
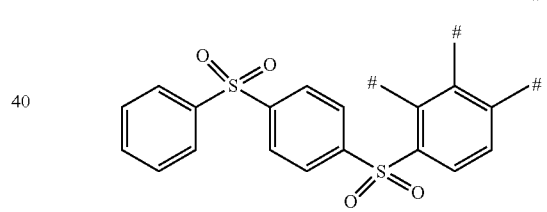
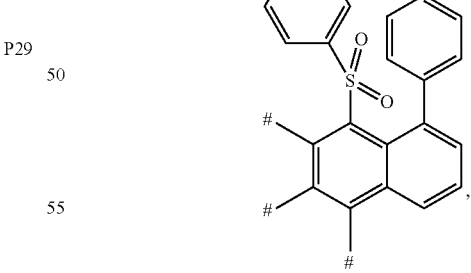
where # represents a position which can be linked to

33
The target compounds with the sulfone substituent as an electron acceptor may be selected from:
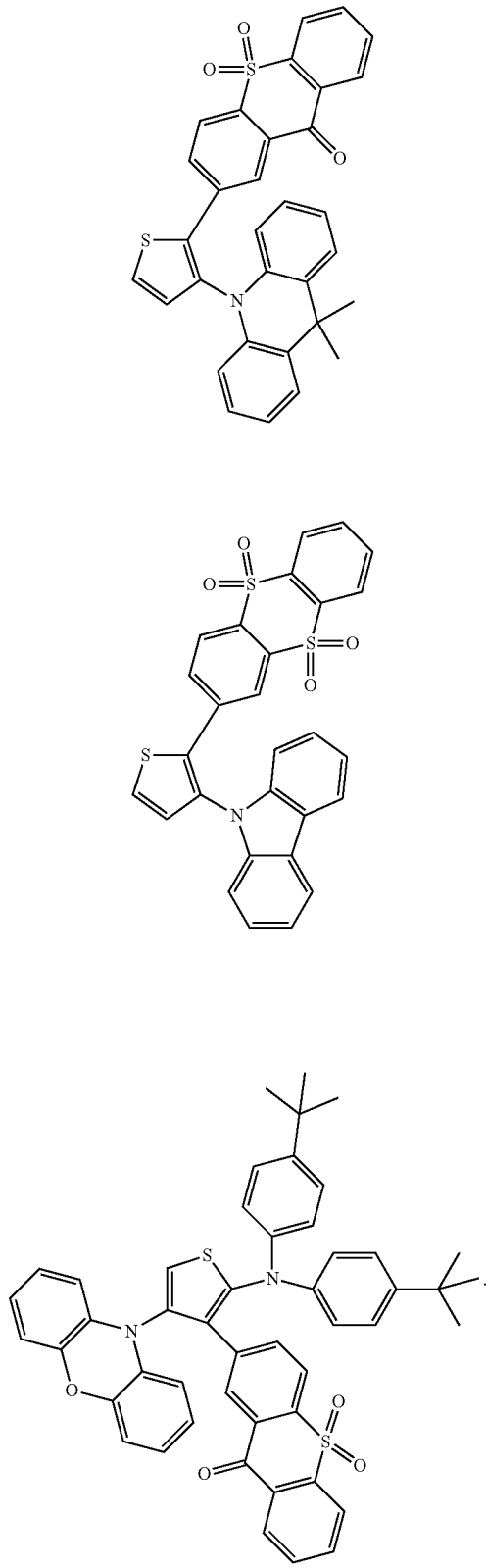
34
According to one embodiment of the present disclosure, the A unit is selected from any one or more of the following structures:
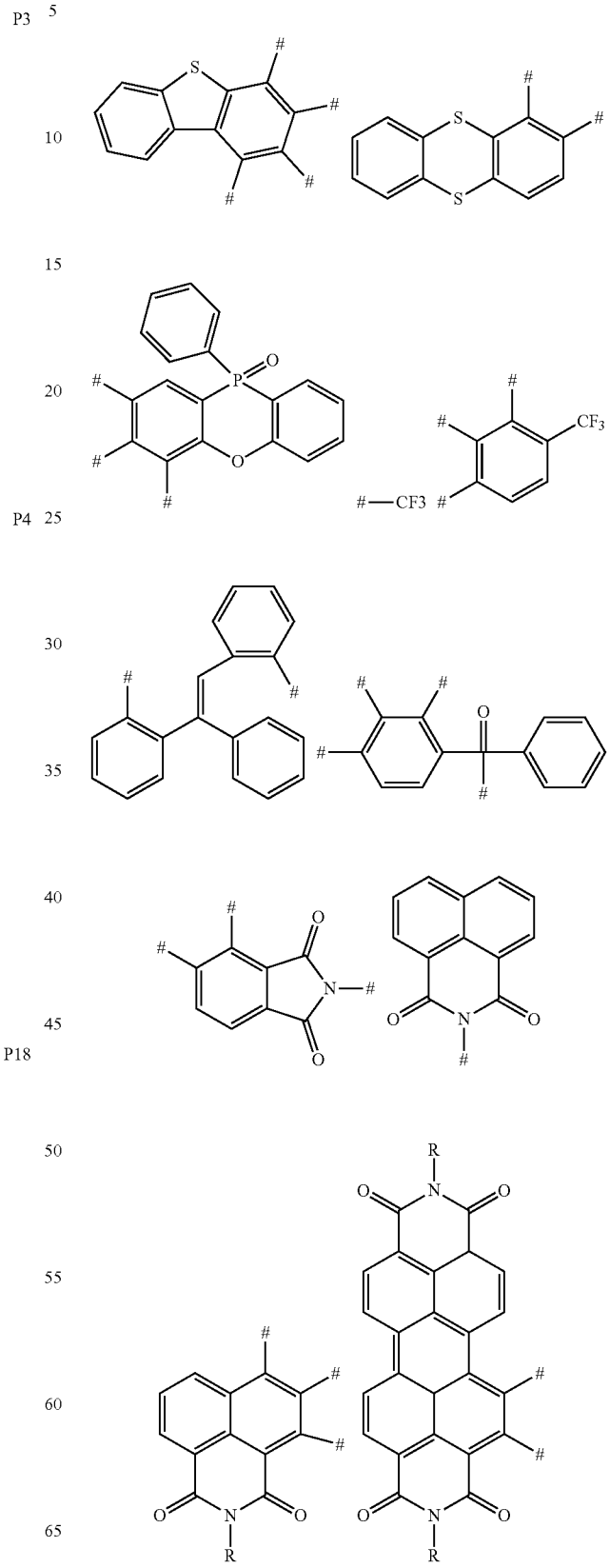

-continued

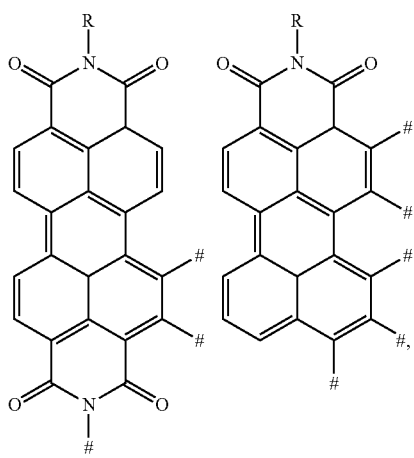

where # represents a position which can be linked to

R in each structural formula independently represents an alkyl group having 1 to 20 carbon atoms, an alkoxy group having 1 to 20 carbon atoms, an alkenyl group having 2 to 20 carbon atoms, an alkynyl group having 2 to 20 carbon atoms, a naphthenic group having 4 to 8 carbon atoms, an aromatic group having 6 to 40 carbon atoms, or a heteromatic group having 4 to 40 carbon atoms.

The target compounds with the above groups as electron acceptors may be selected from:

P12

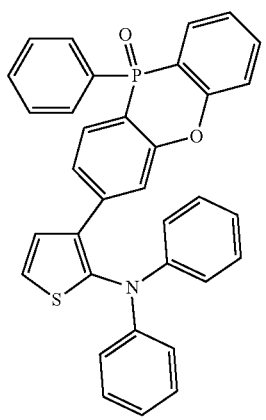

-continued

P31

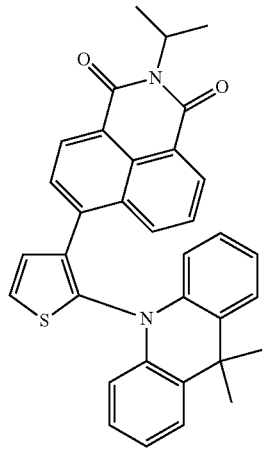

P32

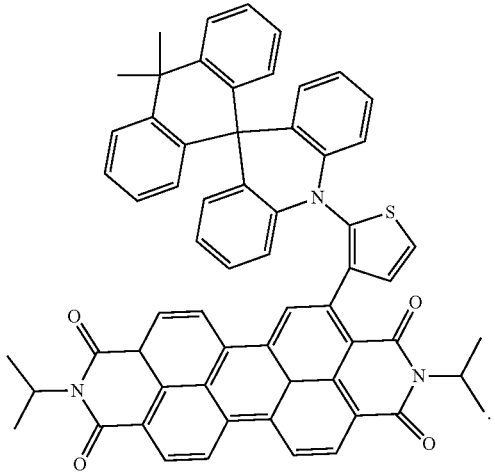

According to one embodiment of the present disclosure, the compound(s) is(are) selected from P1-P32.

According to one embodiment of the present disclosure, the difference between the singlet energy and the triplet energy of the compound is less than 0.3 eV.

The preparation method of the compound according to the present disclosure may include the following steps: reacting an activated thienyl group with a D unit and an A unit, respectively, to obtain the compound.

The preparation methods and results of several specific compounds are described below.

Compound P1
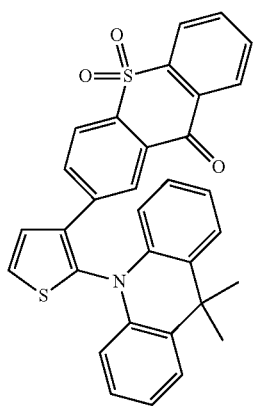
Compound P2
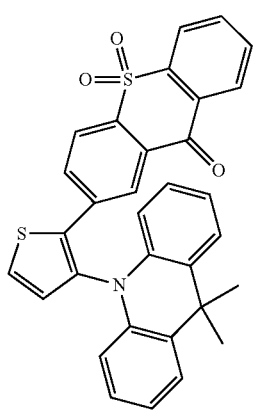
Compound P3
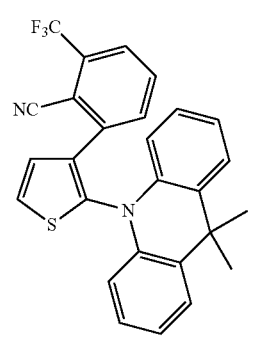
Compound P4
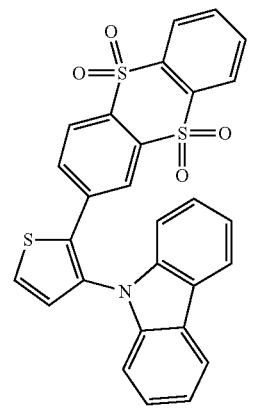
Compound P5
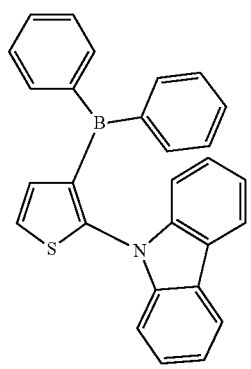
Compound P6
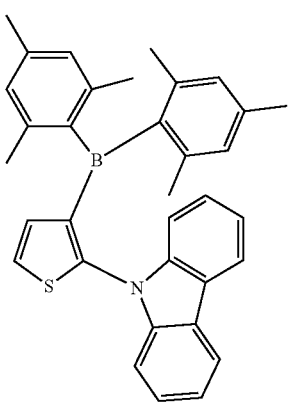
Compound P21
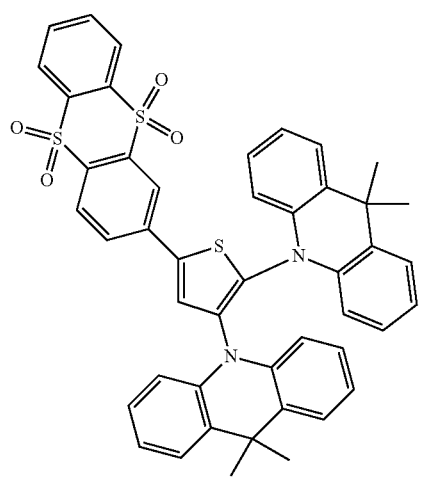

39
-continued

Compound P30

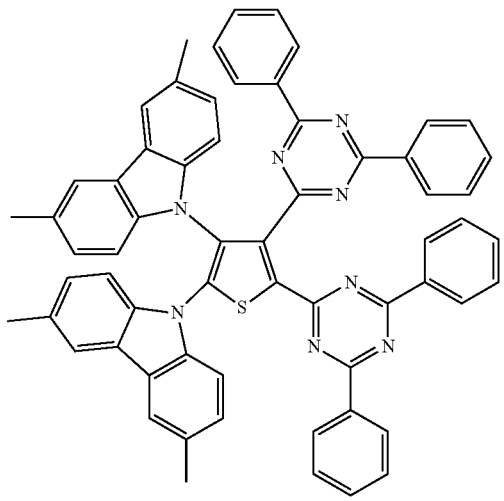

Intermediates S1, S4, S8, S12, S13, S14, S17, S23, S25, S28 and S29 are all commercially available products.

Synthesis of Compound P1
Synthesis of Intermediate S3

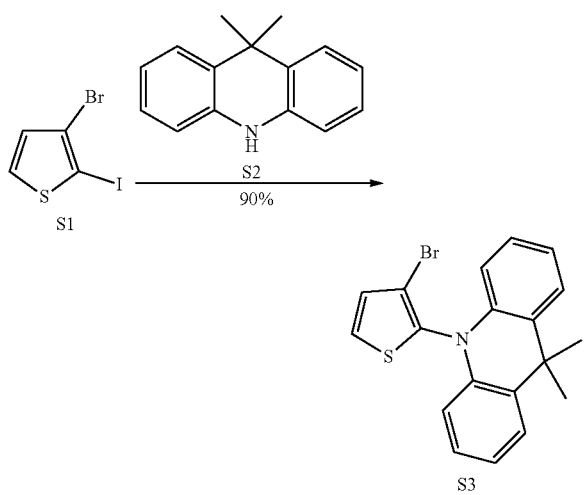

S1 (10 mmol), 9,9-dimethyl-9,10-dihydroacridine S2 (10.5 mmol), (dibenzylideneacetone)dipalladium(0) (0.05 mmol), sodium tert-butoxide (14 mmol), 4,5-bis(diphenylphosphino)-9,9-dimethylxanthene (0.2 mmol) are added to a 50 mL three-necked flask, degassing and nitrogen substitution are carried out rapidly and repeatedly for three times while stirring, and then 20 mL toluene is added through a syringe. Heating reflux of the mixture is carried out under nitrogen atmosphere for 3 hours. After the reaction, water is added to the reaction solution which has been naturally cooled to room temperature, and then the reaction solution is extracted with dichloromethane and washed with saturated brine. After the organic layer is dried with anhydrous sodium sulfate, the solvent is distilled off and then column chromatography for refining is carried out to obtain Intermediate S3 (9 mmol, 90%).

MALDI-TOF MS: m/z calcd for $C_{19}H_{16}BrNS$: 369.0; found: 369.0

40
Synthesis of Intermediate S4

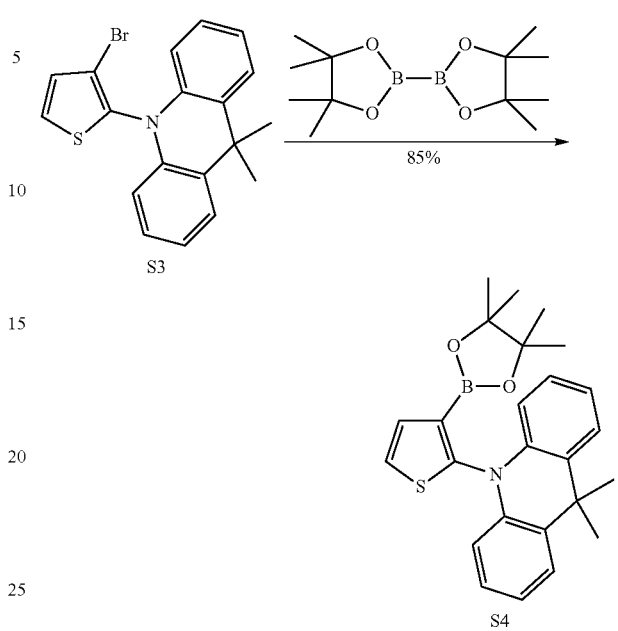

First S3 (30 mmol), bis(pinacolato)diboron (36 mmol), (1,1'-bis(diphenylphosphino)ferrocene)dichloropalladium (II) (0.3 mmol) and potassium acetate (75 mmol) are added to a 250 ml three-necked flask separately, and degassing and nitrogen substitution are carried out rapidly and repeatedly for three times while stirring, and then 100 mL tetrahydrofuran is added through a syringe. Heating reflux of the resulting mixed solution reactant is carried out at a reaction temperature of 80° C. for 5 hours while stirring at a certain speed. After the reaction is completed, the resulting solution is cooled to room temperature, added 100 ml of water, and extracted with ether. The resulting organic phase is dried with anhydrous sodium sulfate, the solvent is distilled off, and column chromatography for refining is carried out to obtain Intermediate S4 (25.5 mmol, 85%).

MALDI-TOF MS: m/z calcd for $C_{25}H_{28}BNO_2S$: 417.2; found:417.2

Synthesis of intermediate S6

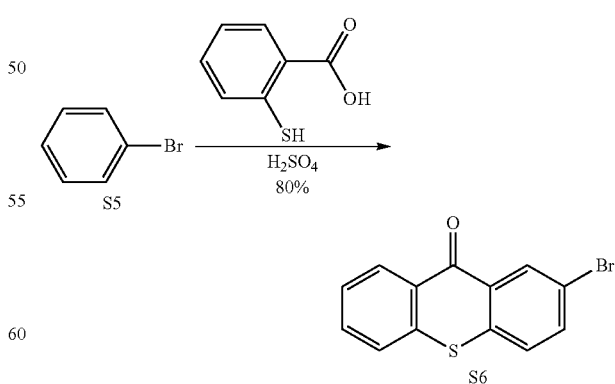

Under room temperature, 20 ml concentrated sulfuric acid is added to a 50 ml single-necked flask, then 6 ml bromobenzene S5 (57 mmol) is added, and stirred for half an hour at room temperature to obtain a white turbid liquid, and then 1.0 g mercaptosalicylic acid (6.5 mmol) is added in portions over a half hour. The resulting solution is stirred at room temperature for 24 hours, then heated at 100° C. for 2-3 hours, cooled to room temperature, carefully poured into ice water, and then suction filtering is carried out to obtain a solid. Then 20% NaOH aqueous solution is added and stirred for 2 hours, and suction filtering is carried out and washing is carried out with water to neutral to obtain a yellow solid S6 (5.2 mmol, 80%).

$^1$H NMR (400 MHz, CDCl$_3$, ppm): 7.70-7.90 (s, 2H), 7.40-7.60 (m, 4H), 7.30 (m, 1H). MALDI-TOF MS: m/z calcd for C$_{13}$H$_7$BrOS: 289.9; found: 290.0

Synthesis of Intermediate S7

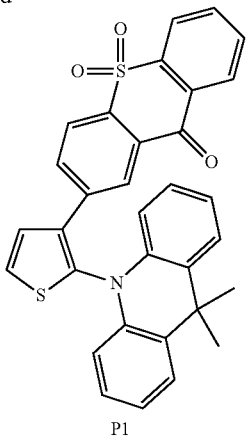

40 mL glacial acetic acid and 20 mL methylene chloride are added to a 50 mL single-necked flask at room temperature, then material intermediate S6 (3 mmol) and 5 times equivalents of 30% hydrogen peroxide are added, and stirred at 55-60° C. for 20-24 hours. After cooling to room temperature, the resulting solution is extracted with dichloromethane and the column chromatography is carried out to obtain a white solid S7 (2.6 mmol, 85%).

MALDI-TOF MS: m/z calcd for C$_{13}$H$_7$BrO$_3$S: 321.9; found: 321.8

Synthesis of Compound P1

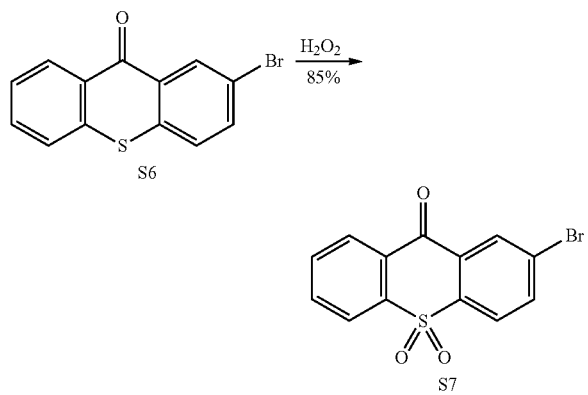

Under the protection of nitrogen, the compounds S4 (25 mmol), S7 (25 mmol), [Pd2(dba)3]·CHCl3 (0.5 mmol) and HP(tBu)$_3$·BF$_4$ (1.0 mmol) are weighed and added to a 250 mL two-necked flask. 100 mL toluene is injected into a two-necked flask (introduce N$_2$ for 15 minutes in advance to remove oxygen), then 12 mL of a 1M K$_2$CO$_3$ aqueous solution is added dropwise (introduce N$_2$ for 15 minutes in advance to remove oxygen) and stirred overnight at room temperature. After the reaction is completed, 100 mL deionized water is added, and then a few drops of 2 M HCl is added. The resulting solution is extracted with dichloromethane, the organic phase is collected and dried with anhydrous Na$_2$SO$_4$. The dried solution is filtered and the solvent is removed by using a rotary evaporator to obtain a crude product. The crude product is purified by silica gel chromatographic column to finally obtain a solid P1 (19.5 mmol, 78%).

MALDI-TOF MS: m/z calcd for C$_{32}$H$_{23}$NO$_3$S$_2$: 533.1; found: 533.0

Calculated values through element analysis: C, 72.02; H, 4.34; N, 2.62; O, 8.99; S, 12.02; test values: C, 72.02; H, 4.33; N, 2.63; O, 8.98; S, 12.03.

Synthesis of Compound P2

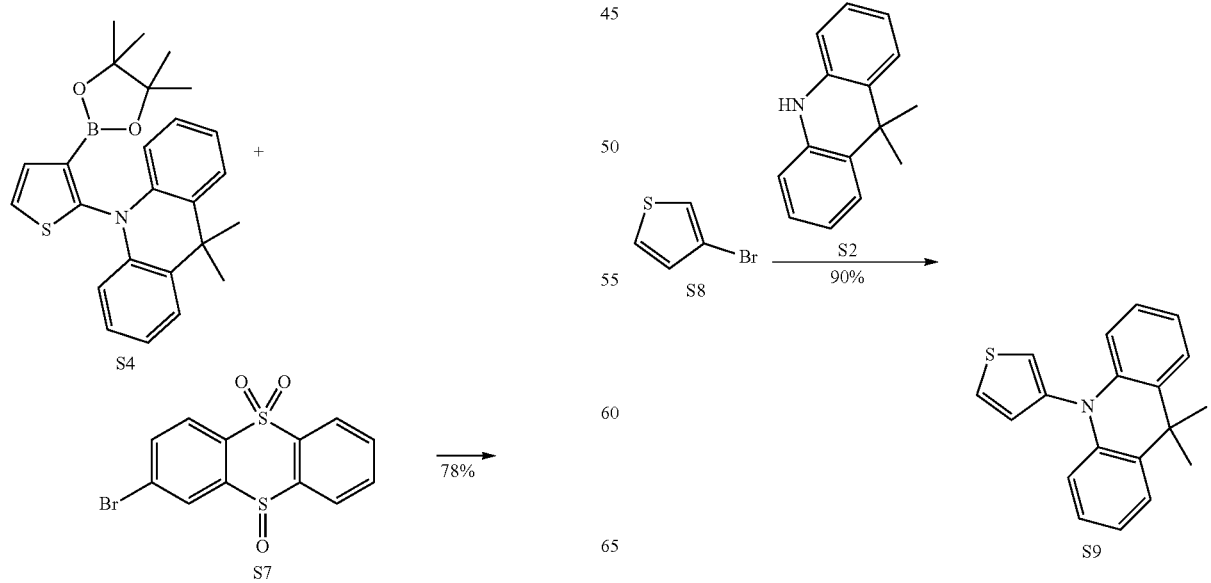

S8 (10 mmol), 9,9-dimethyl-9,10-dihydroacridine S2 (10.5 mmol), (dibenzylideneacetone)dipalladium(0) (0.05 mmol), sodium tert-butoxide (14 mmol), 4,5-bis(diphenylphosphino)-9,9-dimethylxanthene (0.2 mmol) are added to a 50 mL three-necked flask, and degassing and nitrogen substitution are carried out rapidly and repeatedly for three times while stirring, and then 20 mL toluene is added through a syringe. Heating reflux of the mixture is carried out under nitrogen atmosphere for 3 hours. After reaction, water is added to the reaction solution which has been naturally cooled to room temperature, and then the resulting solution is extracted with dichloromethane and washed with saturated brine. After the organic layer is dried with anhydrous sodium sulfate, the solvent is distilled off and then column chromatography for refining is carried out to obtain Intermediate S9 (9 mmol, 90%).

MALDI-TOF MS: m/z calcd for $C_{19}H_{17}NS$: 291.1; found: 291.1

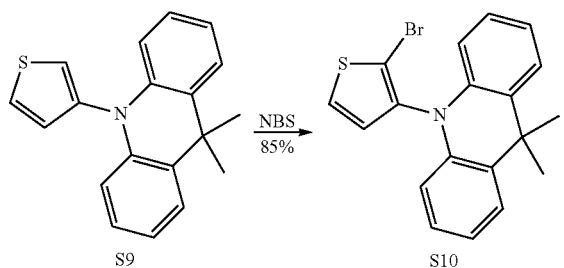

S9 (10 mmol) is weighed and added to a 100 mL two-necked flask, and 30 mL nitrogen-deaerated toluene is added to dissolve S9, one of the two necks is connected to a constant pressure dropping funnel, and the gas in the reaction system is substituted with nitrogen. NBS (10.5 mmol) is weighed, and 20 mL toluene is added to dissolve the NBS, and the toluene solution of NBS is added dropwise to the toluene solution of S9 through the dropping funnel at 0° C. in the absence of light, stirred for 2 hours, and then slowly heated up to room temperature and stirred overnight. After the reaction is completed, 50 mL, deionized water is added to quench the reaction, and the resulting solution is extracted with dichloromethane (100 mL×3), the organic phase is collected, dried with anhydrous $Na_2SO_4$, and filtered and the solvent is distilled off under reduced pressure by using a rotary evaporator to obtain a crude product. The gradient elution and purification of the crude product is carried out through silica gel column chromatography to finally obtain a solid powder S10 (8.5 mmol, 85%).

MALDI-TOF MS: m/z calcd for $C_{19}H_{16}BrNS$: 369.0; found: 369.0

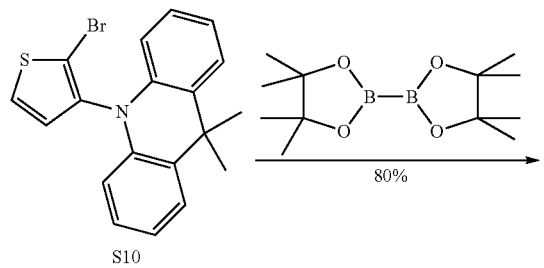

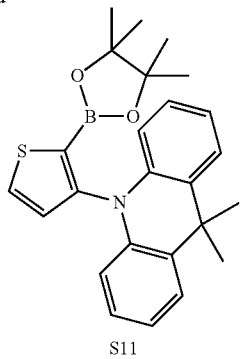

First S10 (30 mmol), bis(pinacolato)diboron (36 mmol), (1,1'-bis(diphenylphosphino)ferrocene)dichloropalladium (II) (0.3 mmol) and potassium acetate (75 mmol) are added to a 250 ml three-necked flask separately, and degassing and nitrogen substitution are carried out rapidly and repeatedly for three times while stirring, and then 100 mL tetrahydrofuran is added through a syringe. Heating reflux of the resulting mixed solution reactant is carried out at a reaction temperature of 80° C. for 5 hours while stirring at a certain rotate speed; after the reaction is completed, the resulting solution is cooled to room temperature, added 100 ml water, and extracted with ether, the resulting organic phase is dried with anhydrous sodium sulfate, the solvent is distilled off, and column chromatography for refining is carried out to obtain Intermediate S4 (24 mmol, 80%).

MALDI-TOF MS: m/z calcd for $C_{25}H_{28}BNO_2S$: 417.2; found: 417.2

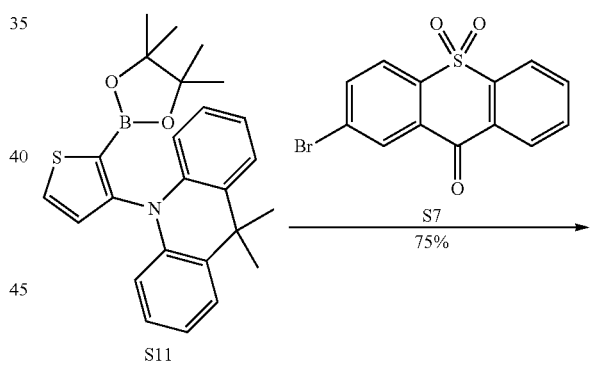

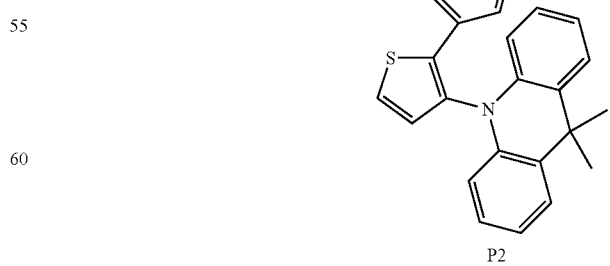

Under the protection of nitrogen, compounds S11 (10 mmol), S7 (10.2 mmol), [Pd2(dba)3]·CHCl3 (0.2 mmol) and HP(tBu)$_3$·BF$_4$ (0.4 mmol) are weighed and then added to a 100 mL, two-necked flask. 30 mL, toluene is injected into a two-necked flask (introduce N$_2$ for 15 minutes in advance to remove oxygen), then 2 mL of a 1M K$_2$CO$_3$ aqueous solution is added dropwise (introduce N$_2$ for 15 minutes in advance to remove oxygen) and stirred overnight at room temperature. After the reaction is completed, 20 mL deionized water is added, then a few drops of 2 M HCl is added; the resulting solution is extracted with dichloromethane, the organic phase is collected and dried with anhydrous Na$_2$SO$_4$. The dried solution is filtered and the solvent is removed by using a rotary evaporator to obtain a crude product. The crude product is purified by silica gel chromatographic column to finally obtain a solid P2 (7.5 mmol, 75%).

MALDI-TOF MS: m/z calcd for C$_{32}$H$_{23}$NO$_3$S$_2$: 533.1; found:533.2 Calculated values through element analysis: C, 72.02; H, 4.34; N, 2.62; O, 8.99; S, 12.02; test values: C, 72.02; H, 4.33; N, 2.63; O, 8.98; S, 12.03.

Synthesis of Compound P3

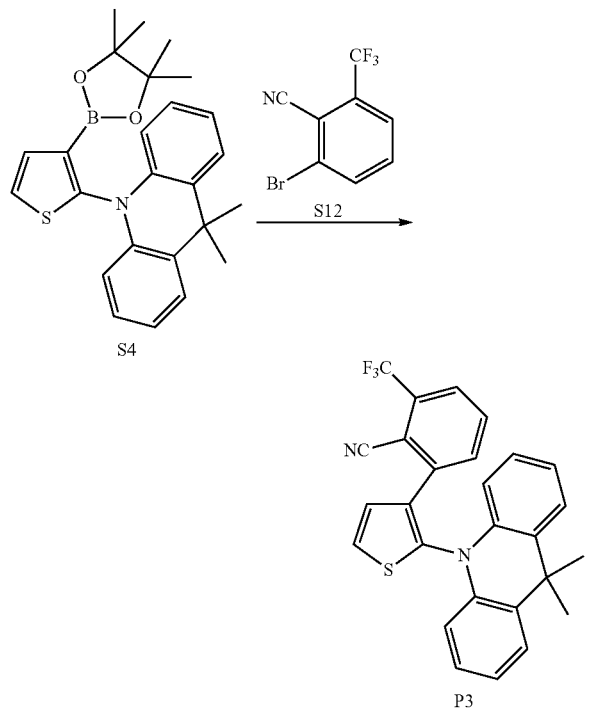

Under the protection of nitrogen, compounds S4 (20 mmol), S12 (20 mmol), [Pd2(dba)3]·CHCl3 (0.4 mmol) and HP(tBu)$_3$·BF$_4$ (0.8 mmol) are weighed and then added to a 250 mL two-necked flask. 100 mL toluene is injected into a two-necked flask (introduce N$_2$ for 15 minutes in advance to remove oxygen), then 12 mL of a 1M K$_2$CO$_3$ aqueous solution is added dropwise (introduce N$_2$ for 15 minutes in advance to remove oxygen) and stirred overnight at room temperature. After the reaction is completed, 100 mL deionized water is added, then a few drops of 2 M HCl is added; the resulting solution is extracted with dichloromethane, the organic phase is collected and dried with anhydrous Na$_2$SO$_4$. The dried solution is filtered and the solvent is removed by using a rotary evaporator to obtain a crude product. The crude product is purified by silica gel chromatographic column to finally obtain a solid P3 (15.6 mmol, 78%).

MALDI-TOF MS: m/z calcd for C$_{27}$H$_{19}$F$_3$N$_2$S: 460.1; found: 460.1

Calculated values through element analysis: C, 70.42; H, 4.16; F, 12.38; N, 6.08; S, 6.96; test values: C, 70.42; H, 4.15; F, 12.39; N, 6.07; S, 6.97.

Synthesis of Compound P4

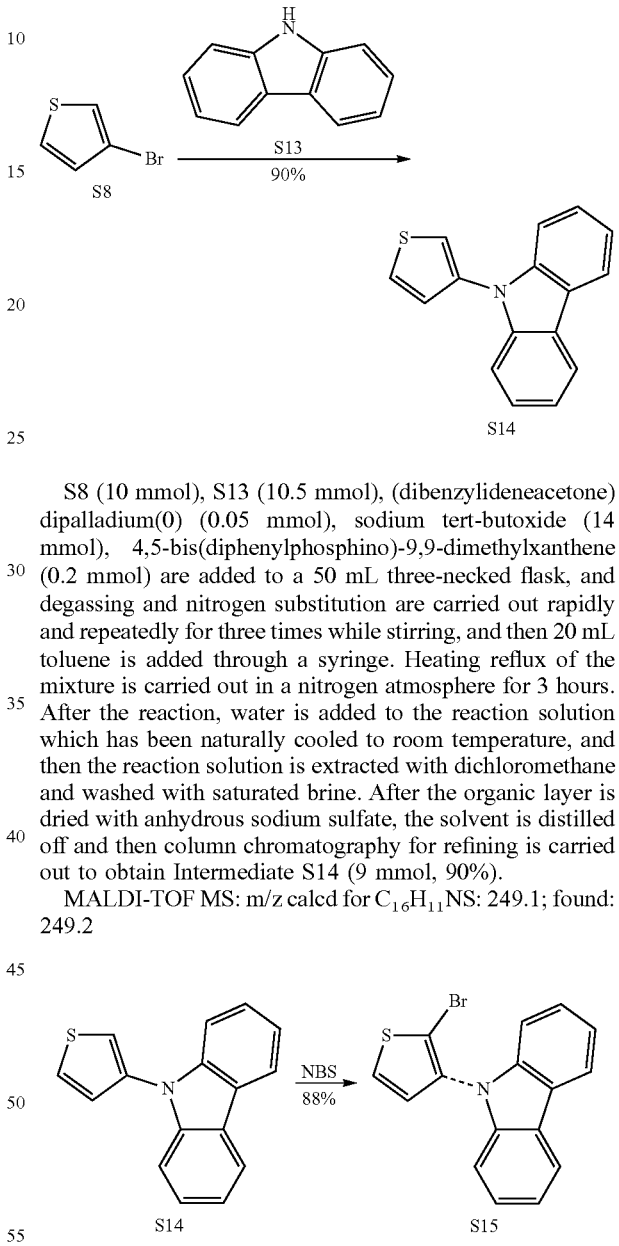

S8 (10 mmol), S13 (10.5 mmol), (dibenzylideneacetone)dipalladium(0) (0.05 mmol), sodium tert-butoxide (14 mmol), 4,5-bis(diphenylphosphino)-9,9-dimethylxanthene (0.2 mmol) are added to a 50 mL three-necked flask, and degassing and nitrogen substitution are carried out rapidly and repeatedly for three times while stirring, and then 20 mL toluene is added through a syringe. Heating reflux of the mixture is carried out in a nitrogen atmosphere for 3 hours. After the reaction, water is added to the reaction solution which has been naturally cooled to room temperature, and then the reaction solution is extracted with dichloromethane and washed with saturated brine. After the organic layer is dried with anhydrous sodium sulfate, the solvent is distilled off and then column chromatography for refining is carried out to obtain Intermediate S14 (9 mmol, 90%).

MALDI-TOF MS: m/z calcd for C$_{16}$H$_{11}$NS: 249.1; found: 249.2

S14 (15 mmol) is weighed and added to a 250 mL two-necked flask, and 50 mL nitrogen-deaerated toluene is added to dissolve S14, one of the two necks is connected to a constant pressure dropping funnel, and the gas in the reaction system substituted with nitrogen. NBS (15.2 mmol) is weighed, 50 mL of toluene is added to dissolve the NBS, and the toluene solution of NBS is added dropwise to the toluene solution of S14 through the dropping tunnel at 0° C. in the absence of light, stirred for 2 hours, and then slowly heated up to room temperature and stirred overnight. After the reaction is completed, 100 mL deionized water is added to quench the reaction, and the resulting solution is extracted with dichloromethane (100 mL×3), the organic phase is collected, dried with anhydrous Na$_2$SO$_4$, and filtered, and the solvent is distilled off under reduced pressure by using a rotary evaporator to obtain a crude product. The gradient elution and purification is carried out on the crude product through silica gel column chromatography to finally obtain a solid powder S15 (13.2 mmol, 88%).

MALDI-TOF MS: m/z calcd for C$_{16}$H$_{10}$BrNS: 327.0; found: 326.9

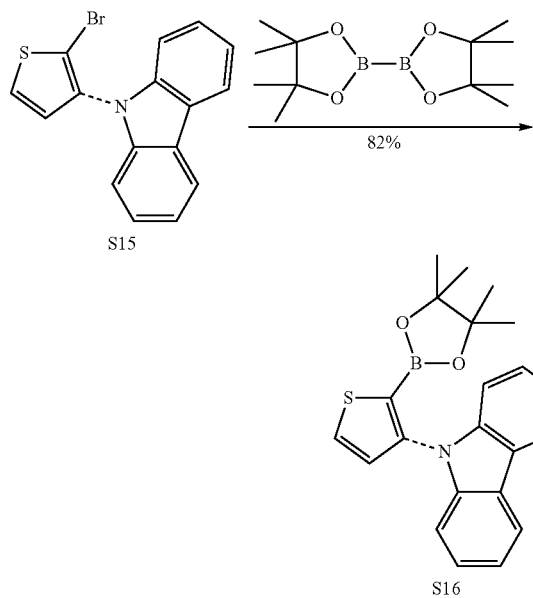

First S15 (30 mmol), bis(pinacolato)diboron (36 mmol), (1,1'-bis(diphenylphosphino)ferrocene)dichloropalladium (II) (0.3 mmol) and potassium acetate (75 mmol) are added to a 250 ml three-necked flask separately, and degassing and nitrogen substitution are carried out rapidly and repeatedly for three times while stirring, and then 100 mL tetrahydrofuran is added through a syringe. Heating reflux of the resulting mixed solution reactant is carried out at a reaction temperature of 80° C. for 5 hours while stirring at a certain rotate speed; after the reaction is completed, the resulting solution is cooled to room temperature, added 100 ml water, and extracted with ether. The resulting organic phase is dried with anhydrous sodium sulfate, the solvent is distilled off, and column chromatography for refining is carried out to obtain Intermediate S16 (24.6 mmol, 82%).

MALDI-TOF MS: m/z calcd for C$_{22}$H$_{22}$BNO$_2$S: 375.2; found: 375.2

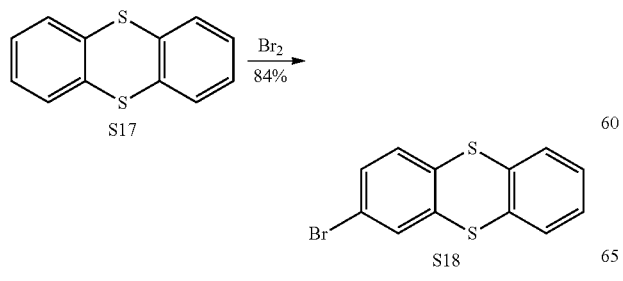

Under the protection of nitrogen, S18 (30 mmol) is weighed, 60 mL acetic acid is added, then 36 mmol liquid bromine is added dropwise while stirring, and then the resulting mixed solution is stirred for 5 hours at 80° C. The excess molecular bromine is quenched with an aqueous solution of NaHSO3, the resulting solution is extracted with dichloromethane (100 mL×3), the organic phase is collected, dried with anhydrous Na$_2$SO$_4$ and filtered, and the solvent is distilled off under reduced pressure by using a rotary evaporator to obtain a crude product. The gradient elution and purification are carried out on the crude product through silica gel column chromatography and finally purification with n-hexane through recrystallization is carried out to obtain a solid powder S18 (25.2 mmol, 84%).

MALDI-TOF MS: m/z calcd for C$_{12}$H$_7$BrS$_2$: 293.9; found: 293.8

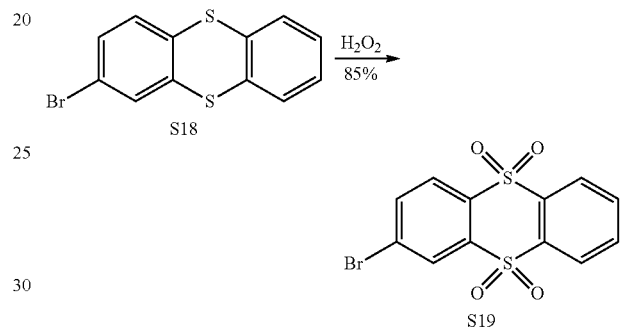

40 mL glacial acetic acid and 20 mL methylene chloride are added to a 50 mL single-necked flask at room temperature, then raw material intermediate S18 (6 mmol) and 5 times equivalents of 30% hydrogen peroxide are added, stirred at 55-60° C. for 20-24 hours, and then cooled to room temperature. The resulting solution is extracted with dichloromethane and column chromatography is carried out to obtain a white solid S9 (5.1 mmol, 85%).

MALDI-TOF MS: m/z calcd for C$_{12}$H$_7$BrO$_4$S$_2$: 357.9; found: 358.0

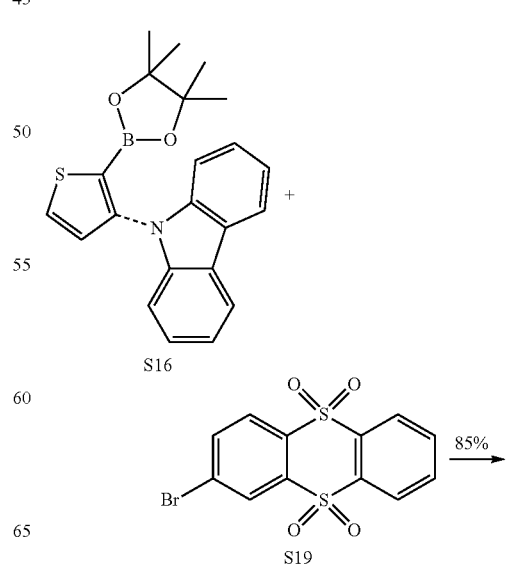

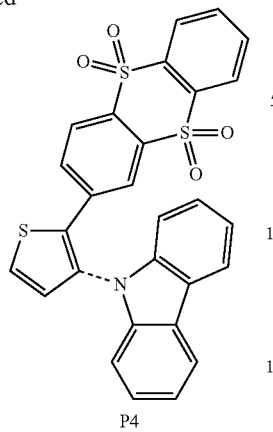

P4

Under the protection of nitrogen, compounds S16 (20 mmol), S19 (20.1 mmol), [Pd2(dba)3]·CHCl3 (0.5 mmol) and HP(tBu)$_3$·BF$_4$ (1 mmol) are weighed and then added to a 250 mL two-necked flask. 100 mL toluene is injected into a two-necked flask (introduce N$_2$ for 15 minutes in advance to remove oxygen), then 12 mL of a 1M K$_2$CO$_3$ aqueous solution is added dropwise (introduce N$_2$ for 15 minutes in advance to remove oxygen) and stirred overnight at room temperature. After the reaction is completed. 50 mL deionized water is added, then a few drops of 2 M HCl is added; the resulting solution is extracted with dichloromethane, the organic phase is collected and dried with anhydrous Na$_2$SO$_4$. The dried solution is filtered and the solvent is removed by using a rotary evaporator to obtain a crude product. The crude product is purified by silica gel chromatographic column to finally obtain a solid P4 (17 mmol, 85%).

MALDI-TOF MS: m/z calcd for C$_{28}$H$_{17}$NO$_4$S$_3$: 527.0; found: 527.1

Calculated values through element analysis: C, 63,74; H, 3.25; N, 2.65; 0, 12.13; S, 18,23; test values: C, 63,74; H, 3.24: N, 2.66; 0, 12.14; S, 18.22.

Synthesis of Compound P5

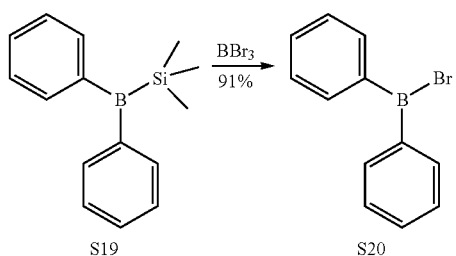

Under the protection of nitrogen, the compound S19 (20 mmol) is weighed and added to a 250 mL two-necked flask and cooled to 0° C. 20 mmol boron tribromide is injected dropwise into a two-necked flask, and slowly heated the resulting mixed solution to room temperature, reacted at 180° C. for 24 hours, cooled to room temperature, and distilled under reduced pressure (bp 120-122° C./0.1 torr) to obtain S20 (18.2 mmol, 91%).

MALDI-TOF MS: m/z calcd for C$_{12}$H$_{10}$BBr: 244.0; found: 244.0

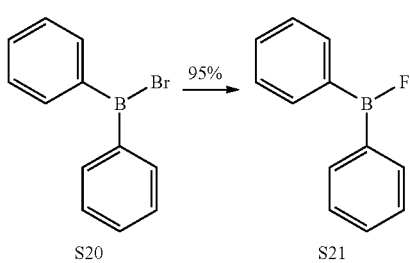 [SMILES: BrB(c1ccccc1)c1ccccc1 ; FB(c1ccccc1)c1ccccc1 ; "S20" ; "S21"]

Under the protection of nitrogen, compound S20 (13 mmol) is weighed and added to a 250 mL two-necked round-bottom flask, KBF4 (28 mmol) is injected dropwise into the two-necked flask and distilled wider reduced pressure to obtain S21 (12.4 mmol, 91%).

MALDI-TOF MS: m/z calcd for C$_{12}$H$_{10}$BF: 184.1; found: 184.0

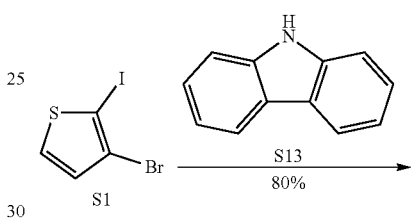

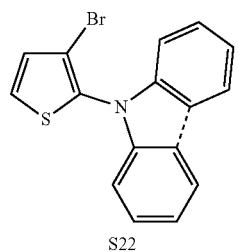

S22

S1 (10 mmol), S13 (10.5 mmol), (dibenzylideneacetone) dipalladium(0) (0.05 mmol), sodium tert-butoxide (14 mmol), 4,5-bis(diphenylpho sphino)-9,9-dimethylxanthene (0.2 mmol) are added to a 50 ml, three-necked flask, and degassing and nitrogen substitution are carried out rapidly and repeatedly for three times while stirring, and then 20 mL toluene is added through a. syringe. Heating reflux of the mixture is carried out in a nitrogen atmosphere for 3 hours. After reaction, water is added to the reaction solution which has been naturally cooled to room temperature, and then the resulting solution is extracted with dichloromethane and washed with saturated brine. After the organic layer is dried with anhydrous sodium sulfate, the solvent is distilled off and then column chromatography for refining is carried out to obtain Intermediate S22 (8 mmol, 80%).

MALDI-TOF MS: m/z calcd for C$_{16}$H$_{10}$BrNS: 327.0; found: 326.9

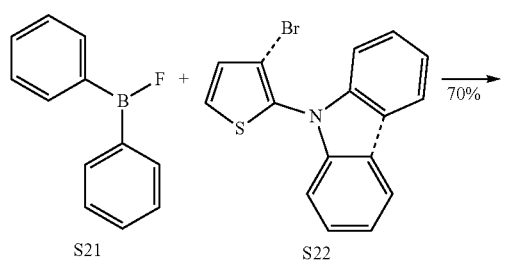

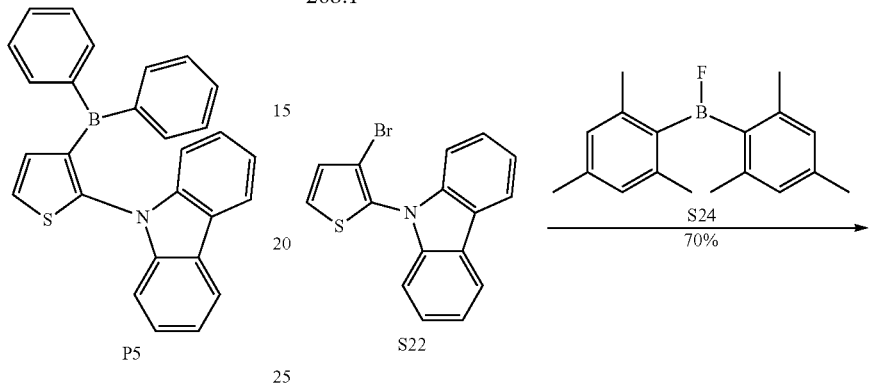

S22 (10 mmol) is weighed and added to a 100 mL two-necked flask and degassing and nitrogen substitution is carried out rapidly and repeatedly for three times while stirring, 40 mL dry ether is added to dissolve S22, n-BuLi solution (10.5 mmol) is added dropwise at −78° C., continuously stirred for 15 min, slowly heated up to room temperature and stirred for 1 hour, cooled down again to −78° C., and the ether solution of S21 (10.2 mmol in 25 mL) is added dropwise, stirred for 30 minutes, slowly heated up to room temperature overnight, and distilled under reduced pressure to remove volatile solvent, and the crude product is washed with methanol (5×10 mL), and finally column chromatography for refining is carried out to obtain the compound P5 (7 mmol, 70%).

MALDI-TOF MS: m/z calcd for $C_{28}H_{20}BNS$: 413.1; found: 413.2

Calculated values through element analysis: C, 81.36; H, 4.88; B, 2.62; N, 3.39; S, 7.76; test values: C, 81.36; H, 489; B, 2.61; N, 3,40; S, 7.75.

Synthesis of Compound P6

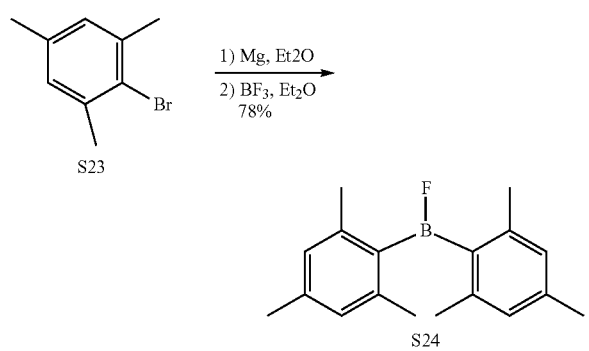

Mg bars (200 mmol) is weighed and added to a 250 mL three-necked flask, and degassing and nitrogen substitution are carried out rapidly and repeatedly for three times while stirring, S23 (200 mmol) and dry tetrahydrofuran (100 mL) are added, heated to initiate a reaction and reacted for 2 hours under a reflux state. The reaction mixture is cooled to 0° C., and an ether solution of boron trifluoride (90 mmol) is added dropwise at 0° C., reflux reaction is carried out again for 2 hour to obtain a suspension of S24 in THF, the suspension is distilled under reduced pressure to remove the solvent, purified by column chromatography, and the solvent is removed using n-hexane as eluent to obtain S24 (156 mmol, 78%).

MALDI-TOF MS: m/z calcd for $C_{18}H_{22}BF$: 268.2; found: 268.1

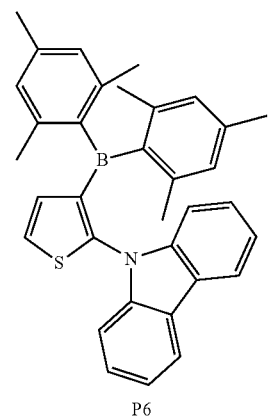

S22 (10 mmol) is weighed and added to a 100 mL two-necked flask, and degassing and nitrogen substitution are carried out rapidly and repeatedly for three times while stirring, 40 mL dry ether is added to dissolve S22, n-BuLi solution (10.5 mmol) is added dropwise at −78° C., continuously stirred for 15 min, slowly heated up to room temperature and stirred for 1 hour, cooled down again to −78° C., the ether solution of S24 (10.2 mmol in 25 mL) is added dropwise stirred for 30 minutes, slowly heated up to room temperature overnight, and distilled under reduced pressure to remove volatile solvent, the crude product is washed with methanol (5×10 mL), and finally column chromatography for refining is carried out to obtain the compound P6 (7 mmol 70%).

MALDI-TOF MS: m/z calcd for $C_{34}H_{32}BNS$: 497.2; found: 497.2

(Calculated values through element analysis: C, 82.08; H, 6.48; B, 2.17; N, 2.82; S, 6.45; test values: C, 82.08; H, 6.49; B, 2.16; N, 2.83; S, 6.44.

Synthesis of Compound P21

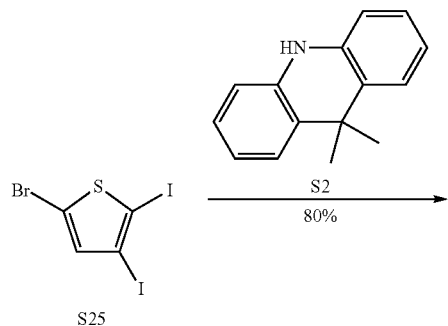

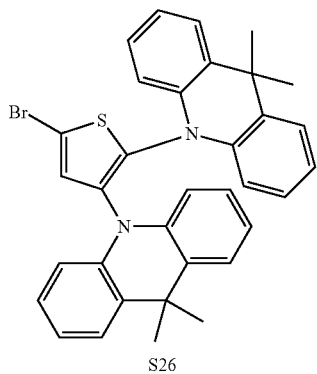

S25 (10 mmol), S2 (20.5 mmol), (dibenzylideneacetone) dipalladium(0) (0.05 mmol), sodium tert-butoxide (14 mmol), 4,5-bis(diphenylphosphino)-9,9-dimethylxanthene (0.2 mmol) are added to a 50 mL three-necked flask, and degassing and nitrogen substitution are carried out rapidly and repeatedly for three times while stirring, and then 20 mL toluene is added through a syringe. Heating reflux of the mixture is carried out in a nitrogen atmosphere for 3 hours. After the reaction, water is added to the reaction solution which has been naturally cooled to room temperature, and then the resulting solution is extracted with dichloromethane and washed with saturated brine. After the organic layer is dried with anhydrous sodium sulfate, the solvent is distilled off and then column chromatography for refining is carried out to obtain Intermediate S26 (8 mmol, 80%).

MALDI-TOF MS: m/z calcd for $C_{34}H_{29}BrN_2S$: 576.1; found: 576.1

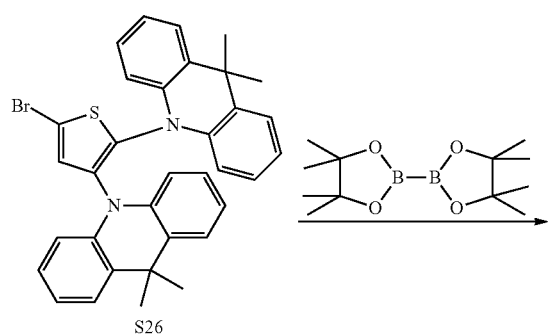

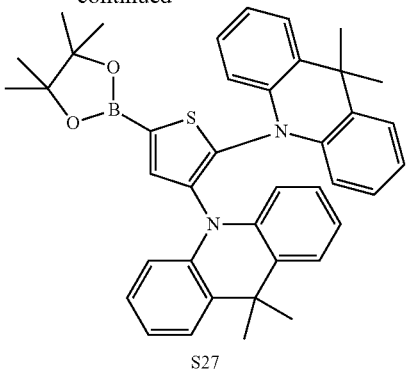

First S26 (30 mmol), bis(pinacolato)diboron (36 mmol), (1,1'-bis(diphenylphosphino)ferrocene)dichloropalladium (II) (0.3 mmol) and potassium acetate (75 mmol) are added to a 250 ml three-necked flask separately, and degassing and nitrogen substitution are carried out rapidly and repeatedly for three times while stirring, and then 100 mL tetrahydrofuran is added through a syringe. Heating reflux of the resulting mixed solution reactant is added at a reaction temperature of 80° C. for 5 hours while stirring at a certain rotate speed; after the reaction is completed, the resulting solution is cooled to room temperature, added 100 ml water, and extracted with ether. The resulting organic phase is dried with anhydrous sodium sulfate, the solvent is distilled off, and column chromatography for refining s carried out to obtain Intermediate S27 (24 mmol, 80%).

MALDI-TOF MS: m/z calcd for $C_{40}H_{41}BN_2O_2S$: 624.3; found: 624.2

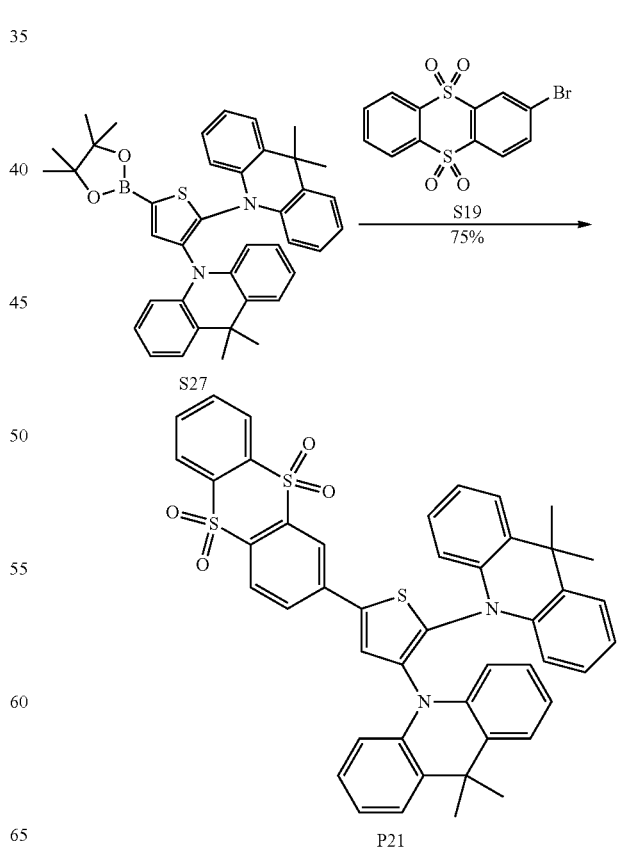

Under the protection of nitrogen, compounds S27 (16 mmol), S19 (16.5 mmol), [Pd2(dba)3]·CHCl3 (0.4 mmol) and HP(tBu)₃BF₄ (0.8 mmol) are weighed and then added to a 250 mL two-necked flask. 100 mL toluene is injected into a two-necked flask (introduce N₂ for 15 minutes in advance to remove oxygen), then 12 mL of a 1M K₂CO₃ aqueous solution is added dropwise (introduce N₂ for 15 minutes in advance to remove oxygen) and stirred overnight at room temperature. After the reaction is completed, 100 mL deionized water is added, then a few drops of 2 M HCl is added. The resulting solution is extracted with dichloromethane, the organic phase is collected and dried with anhydrous Na₂SO₄. The dried solution is filtered and the solvent is removed by using a rotary evaporator to obtain a crude product. The crude product is purified by silica gel chromatographic column to finally obtain a solid P21 (12 mmol, 75%).

MALDI-TOF MS: m/z calcd for $C_{46}H_{36}N_2O_4S_3$: 776.2; found: 776.1

Calculated values through element analysis: C, 55.59; H, 3.65; N, 2.82; O, 6.44; P, 21.82; S, 9,68; test values: C, 55.59; H, 3.66; N, 2.81; O, 6.45; P, 21.82; S, 9.67.

Synthesis of Compound P30

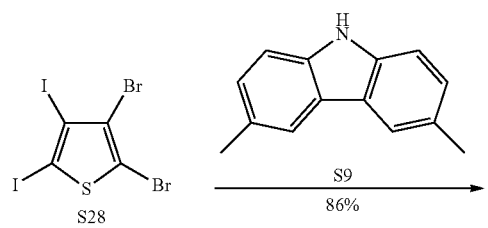

S28 (10 mmol), S29 (21 mmol), (dibenzylideneacetone)dipalladium(0) (0.05 mmol), sodium tert-butoxide (14 mmol), 4,5-bis(diphenylphosphino)-9,9-dimethylxanthene (0.2 mmol) are added to a 250 mL three-necked flask, and degassing and nitrogen substitution are carried out rapidly and repeatedly for three times while stirring, and then 100 mL toluene is added through a syringe. Heating reflux of the mixture is carried out under nitrogen atmosphere for 3 hours. After reaction, water is added to the reaction solution which has been naturally cooled to room temperature, and then the resulting solution is extracted with dichloromethane and washed with saturated brine. After the organic layer is dried with anhydrous sodium sulfate, the solvent is distilled off and then column chromatography for refining is carried out to obtain Intermediate S30 (8.6 mmol, 86%).

MALDI-TOF MS: m/z calcd for $C_{32}H_{24}Br_2N_2S$: 626.0; found: 626.0

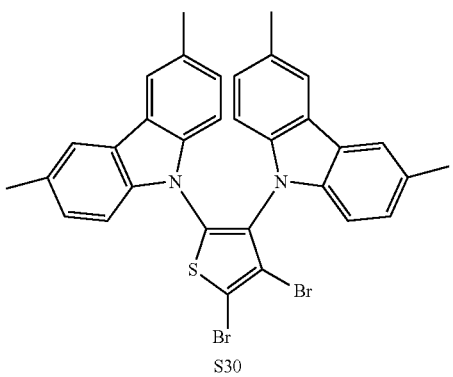

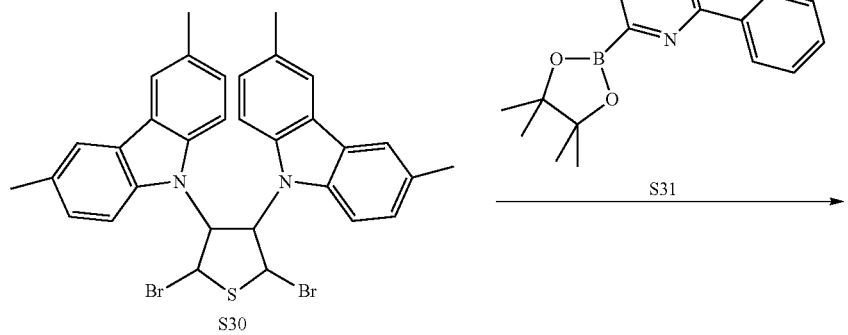

-continued

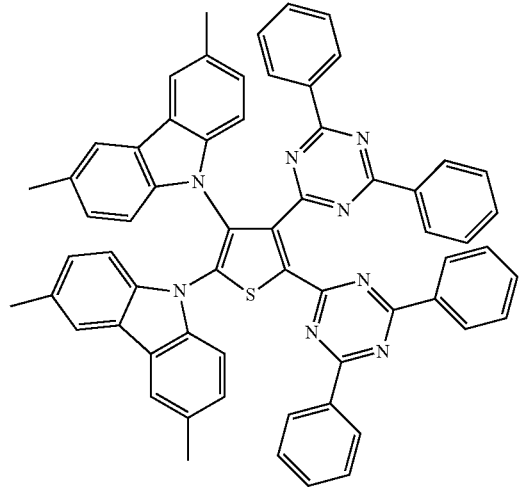

P30

Under the protection of nitrogen, compounds S30 (10 mmol), S31 (21 mmol), [Pd2(dba)3]·CHCl3 (1 mmol) and HP(tBu)$_3$·BF$_4$ (2 mmol) are weighed and then added to a 250 mL two-necked flask. 100 mL toluene is injected into a two-necked flask (introduce N$_2$ for 15 minutes in advance to remove oxygen), then 12 mL of a 1M K$_2$CO$_3$ aqueous solution is added dropwise (introduce N$_2$ for 15 minutes in advance to remove oxygen) and stirred overnight at room temperature. After the reaction is completed, 100 mL deionized water is added, then a few drops of 2 M HCl is added. The resulting solution is extracted with dichloromethane, the organic phase is collected and dried with anhydrous Na$_2$SO$_4$. The dried solution is filtered and the solvent is removed by using a rotary evaporator to obtain a crude product. The crude product is purified by silica gel chromatographic column and finally purification is carried out to obtain a solid P30 (7.5 mmol, 75%).

MALDI-TOF MS: m/z calcd for C$_{62}$H$_{44}$N$_8$S: 932.3; found: 932.4

Calculated values through element analysis: C, 79,80; H, 4.75; N, 12.01; S, 3.44; test values: C, 79.80; H, 4.77; N, 12.00; S, 3.43.

According to another embodiment of the present disclosure, further provided is an organic light emitting display device, including an organic electroluminescent device, and the organic electroluminescent device includes: an organic functional layer, where the organic functional layer includes one or more organic film layers, and at least one of the organic film layers is a light emitting layer; the light emitting layer includes a light emitting material, and the light emitting material includes any one or more of the above compounds.

The organic electroluminescent device further includes: a substrate; a first electrode arranged on the substrate; and a second electrode arranged on the organic functional layer, the organic functional layer is arranged on the first electrode.

According to one embodiment of the present disclosure, the compound functions as a host material or a dopant material of the light emitting layer, or the compound constitutes the light emitting layer alone to prepare a non-doping organic light emitting display device.

According to an implementation of the present disclosure, the compound functions as a red light emitting material of the light emitting layer, and the singlet energy of the red light emitting material is located between 1.61 eV and 1.99 eV; in some embodiments, the singlet ilk energy of the red light emitting material is located between 1.90 eV and 1.98 eV.

According to an implementation of the present disclosure, the compound functions as a green light emitting material of the light emitting layer, and the singlet energy of the green light emitting material is located between 2.15 eV and 2.52 eV; in some embodiments, the singlet energy of the green light emitting material is located between 2.25 eV and 2.35 eV.

According to an implementation of the present disclosure, the compound functions as a blue light emitting material of the light emitting layer, and the singlet energy of the blue light emitting material is located between 2.52 eV and 2.73 eV; in some embodiments, the singlet energy of the blue light emitting material is located between 2.65 eV and 2.71 eV.

According to an embodiment of the present disclosure, the compound functions as a guest material of a light emitting material, and a host material is any one or more of 2,8-bis(diphenylphosphinyloxy)dibenzothiophene (PPT), 4,4'-di (9-carbazolyl) biphenyl (CBP), 3,3'-bis(N-carbazolyl)-1,1'-biphenyl (mCBP), 2,8-bis(diphenylphosphinyloxy)bis benzofuran (PPF), bis(4-(9H-carbazolyl-9-yl)phenyl)diphenylsilane (SiCz), 9-(4-t-butylphenyl)-3,6-bis(triphenylsilyl)-9h-carbazole (CzSi), bis(2-diphenylphosphine oxide)diphenyl ether (DPEPO), 1,3-bis[3,5-bis(pyridin-3-yl)phenyl]benzene (BMPYPB), 4,6-bis(3,5-bis(3-pyridyl)phenyl)-2-methylpyrimidine (B3PYMPM), 9-(3-(9H-carbazolyl-9-yl)phenyl)-9H-carbazole-3-cyano (mCPCN), 9-phenyl-9-[4-(triphenylsilyl)phenyl]-9H-fluorene (TPSi—F), 1,3,5-tris(1-phenyl-1H-benzimidazol-2-yl)benzene (TPBI), diphenyl[4-(triphenylsilyl)phenyl]phosphine oxide (TSPO1), 4,4',4"-tris(carbazolyl-9-yl)triphenylamine (TCTA), 2,6-dicarbazole-1,5-pyridine (26 mCPy), polyvinylcarbazole (PVK) and polyfluorene (PFO). The difference between the HOMO of the host material and the HOMO of the guest material is less than 0.6 eV, or the difference between the LUMO of the host material and the LUMO of the guest material is less than 0.6 eV. According to one embodiment of the present disclosure, the singlet energy of the host material is higher than the singlet energy of the guest material, and the difference between the singlet energy of the host material and the singlet energy of the guest material is less than 1.0 eV.

According to one embodiment of the present disclosure, the compound functions as a host material of a light emitting material, and a guest material is selected from fluorescent materials (e.g., BczVBi, coumarin-6, DCJTB, etc.), TADF materials, or phosphorescent light emitting materials, and the difference between the HOMO of the host material and the HOMO of the guest material is less than 0.6 eV, or the difference between the LUMO of the host material and the LUMO of the guest material is less than 0.6 eV.

According to one embodiment of the present disclosure, the compound functions as a host material of a light emitting material, and a guest material is selected from fluorescent materials (e.g., BczVBi, coumarin-6, DCJTB, etc.) or TADF materials; the singlet energy of the guest material is less than the singlet energy of the host material, and the difference between the singlet energy of the host material and the singlet energy of the guest material is less than 1.0 eV.

According to one embodiment of the present disclosure, the compound functions as a host material of a light emitting material, and a guest material is selected from phosphorescent materials; the triplet energy of the guest material is less than the triplet energy of the host material, and the difference between the triplet energy of the host material and the triplet energy of the guest material is less than 1.0 eV.

According to one embodiment of the disclosure, the light emitting material is a TADF material.

The organic functional layer according to the present disclosure further includes a hole injection layer (HIL), a hole transport layer (HTL), an electron blocking layer (EBL), a hole blocking layer (HBL), an electron transport layer (ETL), and an electron injection layer (EIL).

The hole injection material, the hole transport material and the electron blocking material may be selected from N,N'-diphenyl-N,N'-(1-naphthyl)-1,1'-biphenyl-4,4'-diamine (α-NPD), 4,4',4"-tris(carbazol-9-yl)triphenylamine (TCTA), 1,3-dicarbazol-9-ylbenzene (mCP), 4,4'-bis(9-carbazole) biphenyl (CBP), 3,3'-bis(N-carbazolyl)-1,1'-biphenyl (mCBP), 2,3,6,7,10,11-hexacyano-1,4,5,8,9,12-hexaazatriphenylene (HATCN), 4,4'-cyclohexylbis[N,N-bis(4-methylphenyl) aniline (TAPC), N,N'-diphenyl-N,N'-(1-naphthyl)-1,1'-biphenyl-4,4'-diamine (α-NPB), N,N'-di(naphthalin-2-yl)-N,N'-di(phenyl)biphenyl-4,4'-diamine (NPB), poly(3,4-ethylenedioxythiophene)-polystyrenesulfonic acid (PEDOT:PSS), polyvinylcarbazole (PVK), 9-phenyl-3,9-dicarbazole (CCP), molybdenum trioxide ($MoO_3$) and other materials, but not limited to the above materials.

The hole blocking material, the electron transport material and the electron injection material may be selected from 2,8-bis(diphenylphosphinyloxy)dibenzothiophene (PPT), TSPO1, TPBi, 2,8-bis(diphenylphosphinyloxy)dibenzofuran bis(2-diphenylphosphine oxide)diphenyl ether (DPEPO), lithium fluoride (LiF), 4,6-bis(3,5-bis(3-pyridinyl)phenyl)-2-methylpyrimidine (B3PYMPM), 4,7-diphenyl-1,10-phenanthroline (Bphen), 1,3,5-tris[(3-pyridyl)-3-phenyl]benzene (TmPyBP), tris[2,4,6-trimethyl-3(3-pyridyl)phenyl]borane (3TPYMB), 1,3-bis(3,5-dipyridin-3-ylphenyl)benzene (B3PYPB), 1,3-bis[3,5-bis(pyridin-3-yl)phenyl]benzene (BMPYPHB), 2,4,6-tris(biphenyl-3-yl)-1,3,5-triazine (T2T), diphenylbis[4-(pyridin-3-yl)phenyl]silane (DPPS), cesium carbonate (Cs2O3), bis(2-methyl-8-hydroxyquinoline-N1,O8)-(1,1'-biphenyl-4-hydroxy)aluminum (BAlq), 8-hydroxyquinoline-lithium (Liq), tris(8-hydroxyquinoline) aluminum ($Alq_3$) and other materials, but not limited to the above materials.

The anode material according to the present disclosure may be a metal, such as Cu, Au, Ag, Fe, Cr, Ni, Mn, Pd, Pt, etc.; the anode material may be a metal oxide, such as indium oxide, zinc oxide, indium tin oxide (ITO), indium zinc oxide (IZO), etc.; the anode material may be an alloy; the anode material may be a conductive polymer, such as polyaniline, polypyrrole, poly(3-methylthiophene), and the like. In addition to the above materials and combinations thereof that facilitate hole injection, other known materials suitable for an anode may also be used.

The cathode material according to the present disclosure may be a metal such as Al, Mg, Ag, Im, Sn, Ti, etc.; the cathode material may be an alloy, such as Mg/Ag; the cathode material may be a composite material of a metal and an inorganic compound, such as a multilayered metal material —LiF/Al, $LiO_2$/Al, $BaF_2$/Al, and the like. In addition to the above materials and combinations thereof that facilitate electron injection, other known materials suitable for a cathode may also be used.

The substrate according to the present disclosure may be a rigid substrate (borosilicate glass, float soda-lime glass, high refractive index glass, stainless steel, etc.) or a flexible substrate (e.g., a polyimide (PI) plastic substrate, a polyethylene terephthalate (PET) plastic substrate, a polyethylene naphthalate (PEN) plastic substrate, a polyether sulfone (PES) resin substrate, a polycarbonate (PC) plastic substrate, a ultra-thin flexible glass substrate, a metal foil substrate, etc.).

Vapor Deposition Preparation Process of the Organic Electroluminescent Device

An anode substrate having an ITO film with a film thickness of 100 nm is ultrasonically cleaned with distilled water, acetone, and isopropyl and dried in an oven, the surface is treated with UV for 30 minutes, and then transferred to a vacuum vapor deposition chamber. Vapor deposition of each layer film is started at a vacuum degree of 2×10 HNTCN is vapor-deposited with a thickness of 5 nm to form a hole injection layer, and N,N'-diphenyl-N,N'-(1-Naphthyl)-1,1'-biphenyl-4,4'-diamine (α-NPD) is vapor-deposited with a thickness of 40 nm, and then 4,4',4"-tris(carbazole-9-yl) triphenylamine (TCTA) is vapor-deposited with a thickness of 10 nm to form a hole transport layer (HTL). On the hole transport layer, the target compound of the present disclosure is used as a doping material of the light emitting layer, and 3,3'-bis(N-carbazolyl)-1,1'-biphenyl (mCBP) is used as a host material of the light emitting layer. The doping material and the host material are vapor-deposited at the same time to form a light emitting layer with a thickness of 30 nm.

Diphenyl[4-(triphenylsilyl)phenyl]phosphine oxide (TSPO1) is vapor-deposited on the light emitting layer to form a hole blocking layer (HBL) with a thickness of 5 nm. 4,7-diphenyl-1,10-phenanthroline (Bphen) is vapor-deposited on the hole blocking layer to form an electron transport layer (ETL) with a thickness of 30 nm. On the electron transport layer, 2.5 nm thick LIF and 100 nm thick Al are vapor-deposited in sequence as an electron injection layer (EIL) and a cathode to thus make an organic photoelectric device.

The organic electroluminescent device may also be prepared by solution processing method.

A non-doping device is prepared by the following specific steps: ultrasonically cleaning the ITO glass with acetone, alkaline washing solution, ultrapure water, and isopropyl alcohol in sequence, twice with each, each 15 minutes and then treating with an ozone cleaner for 15 minutes; spin-coating a 40 nm thick PEDOT:PSS solution on a glass substrate; placing in a vacuum oven and drying off at 120° C. for 45 minutes; preparing a TAPC layer and an mCP layer respectively on the PEDOT:PSS to function as a hole transport layer and an electron blocking layer; and then coating with a toluene solution of the compound according to the present disclosure (with concentration of 12 mg/mL) to function as a light emitting layer with a thickness of 40 nm; transferring the substrate to a vacuum chamber for thermal evaporation coating to prepare an electron transport layer (TmPyPb, 50 nm), an electron injection layer (LiF, 0.5-1 nm), and a cathode (Al, 100 nm) to form a complete device.

A doping device is further prepared by the following steps: preparing a o-dichlorobenzene solution (with a concentration of 12 mg/mL) of the host light emitting material and the guest light emitting material respectively, and removing 50 uL (5%) guest material solution by using a pipette and then adding to the host material solution, magnetically stirring to be uniform and then coating the light emitting layer. All other steps are the same as those for preparing the non-doping device.

In some embodiments, the solution processing method is ink-jet printing method.

Figure 2:
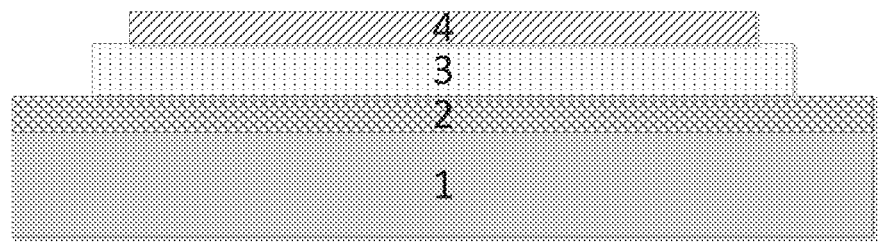
FIG. 2 is a schematic structural diagram of an organic electroluminescent device according to the present disclosure.

The structure of the organic electroluminescent device according to the present disclosure is shown in FIG. 2. The substrate 1 is glass or other suitable material (such as plastic); the first electrode 2 is a transparent electrode such as ITO or IGZO; the organic functional layer 3 includes one or more organic film layers; the second electrode 4 is a metal cathode. The first electrode 2 and the second electrode 4 herein are interchangeable, i.e., the first electrode 2 is a metal cathode, and the second electrode 4 is a transparent electrode such as ITO or IGZO.

Figure 3:
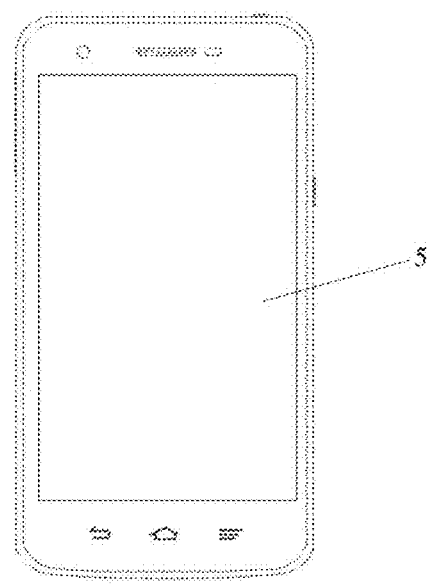
FIG. 3 is a schematic diagram of a mobile phone display screen.

The organic light emitting display device according to the present disclosure may be, for example, a mobile phone display screen, a computer display screen, a liquid crystal television display screen, etc., and regarding this, the embodiment is not particularly limited. FIG. 3 is a schematic diagram of a mobile phone display screen, where 5 denotes a display screen.

It can be seen that there are many optional factors for the compound and the organic light emitting display device according to the present disclosure, and different examples can be combined according to the claims of the present disclosure. The examples of the present disclosure are merely a detailed description of the present disclosure and are not intended to limit the present disclosure. The present disclosure will be further described below with reference to organic electroluminescent devices containing the compounds of the present disclosure as examples.

EXAMPLES 1~8

FIG. 1 shows an orbital distribution of compound 1, where FIG. 1(A) shows the HOMO energy level distribution of compound P1, and FIG. 1(B) shows the LUMO energy level distribution of compound P1. It can be clearly seen from FIG. 1 that the HOMO and LUMO of the compound P1 are respectively arranged on different units to achieve complete separation, which facilitates the reduction of the inter-system energy difference $\Delta E_{ST}$, thereby improving the ability of reverse inter-system crossing.

Based on the density functional theory (DFT), the distribution of molecular frontier orbits is optimized and computed for compounds P1-P6, P21 and P30 using the Gaussian 09 software package at the B3LYP/6-31G(d) computing level. Meanwhile, based on the time-dependent density functional theory (TDDFT), the singlet energy level $S_1$ and the triplet energy level $T_1$ of the molecule is subjected to analog computation.

The relevant data of examples 1~8 are shown in Table 1. From Table 1, it can be seen that the $\Delta E_{ST}$ of all compounds is less than 0.3 eV, which achieves a small difference between singlet and triplet energy levels; moreover, the fluorescence lifetime of all compounds is at the order of microsecond, with significant delayed fluorescence effect. (In Table 1, $S_1$ represents the singlet energy level, $T_1$ represents the triplet energy level, $\Delta E_{ST}$ represents the difference between the singlet and triplet energy levels, and Eg represents the HOMO-LUMO energy level difference.)

TABLE 1

Relevant property data of Compounds P1-P6, P21 and P30

| Example | Compound | HOMO (ev) | LUMO (ev) | $S_1$ (ev) | $T_1$ (ev) | $\Delta E_{ST}$ (ev) | Eg (ev) |
|---|---|---|---|---|---|---|---|
| 1 | P1 | −5.88 | −3.62 | 2.59 | 2.32 | 0.27 | 2.26 |
| 2 | P2 | −5.87 | −3.66 | 2.51 | 2.30 | 0.21 | 2.21 |
| 3 | P3 | −5.88 | −3.06 | 3.06 | 2.95 | 0.11 | 2.82 |
| 4 | P4 | −6.18 | −3.37 | 2.99 | 2.95 | 0.04 | 2.81 |
| 5 | P5 | −5.96 | −3.01 | 2.92 | 2.64 | 0.28 | 2.95 |
| 6 | P6 | −5.98 | −2.91 | 2.69 | 2.62 | 0.07 | 3.07 |
| 7 | P21 | −6.15 | −3.62 | 2.97 | 2.94 | 0.03 | 2.53 |
| 8 | P30 | −5.51 | −3.27 | 2.81 | 2.76 | 0.05 | 2.24 |

Devices Prepared through Vacuum Vapor Deposition

Using compounds P1-P6, P21 and P30 as light emitting materials, non-doping devices N1 to N8 are designed with the following structures: ITO (100 nm)/α-NPD (40 nm)/TCTA (10 nm)/P (40 nm)/TmPyPb (50 nm)/LiF (0.5 nm)/Al (100 nm), and the results are shown in Table 2

TABLE 2

Property results of non-doping devices prepared by vacuum vapor deposition (P1-P6, P21, P30 as light emitters)

| Device | $V_{on}$ [V] | $CE_{(10\ mA/cm^2)}$ (cd A$^{-1}$) | $EQE_{(max)}$ (%) |
|---|---|---|---|
| N1 | 2.78 | 8.5 | 6.8 |
| N2 | 3.12 | 8.6 | 7.2 |
| N3 | 2.76 | 7.5 | 6.7 |
| N4 | 2.95 | 9.4 | 7.8 |
| N5 | 2.72 | 7.2 | 5.8 |
| N6 | 2.95 | 8.0 | 6.8 |
| N7 | 2.78 | 8.4 | 7.5 |
| N8 | 2.62 | 7.5 | 6.3 |

Using P1-P6, P21, and P30 as fluorescent dopants and CBP as host material, doping devices N9 to N16 are designed with the structure: ITO(100 nm)/α-NPD (40 nm)/TCTA (10 nm)/CBP: P (40 nm)/TmPyPb (50 nm)/LiF (0.5 nm)/Al (100 nm). Also, as control, using BCzVBi as a fluorescent dopant and CBP as a host material, a doping device C1 is designed with a structure of ITO (100 nm)/α-NPD (40 nm)/TCTA (10 nm)/CBP: BCzVBi (40 nm, 5%)/TmPyPb (50 nm)/LiF (0.5 nm)/Al (100 nm), and the results are shown in Table 3.

It can be seen from Table 3 that in comparison with the reference device C1 using the classic blue light emitting material BCzVBi as the fluorescent dopant, the $EQE_{S(max)}$ of the N9-N16 (doping) devices are significantly higher than that of the reference device. Due to the TADF property of P1-P6, P21 and P30, the triplet excitons whose transitions are blocked in the conventional fluorescent molecules (such as BCzVBi) can be used to emit light, thereby improving the device efficiency.

TABLE 3

Property results of doping devices prepared by vacuum vapor deposition (using P1-P6, P21 and P30 as fluorescent dopants)

| Device | $V_{on}$ [V] | $CE_{(10\ mA/cm^2)}$ (cd A$^{-1}$) | $EQE_{(max)}$ (%) |
|---|---|---|---|
| N9 | 3.20 | 16.8 | 12.3 |
| N10 | 3.25 | 17.5 | 12.8 |
| N11 | 3.18 | 16.4 | 13.7 |
| N12 | 3.06 | 20.5 | 14.4 |
| N13 | 3.45 | 17.0 | 12.5 |
| N14 | 2.98 | 19.2 | 14.3 |
| N15 | 3.65 | 18.8 | 12.4 |
| N16 | 3.20 | 19.5 | 14.5 |
| C1 | 5.2 | 6.0 | 4.5 |

From Table 2 and Table 3, it can be seen that the devices fabricated through non-doped vacuum vapor deposition with P1-P6, P21 and P30 as light emitting materials have a maximum external quantum efficiency of 7.8%. It indicates that due to the introduction of the thiophene group, the interaction between the D unit and the A unit in the molecule becomes stronger, and the molecular twisting strength increases, and a larger dihedral angle is formed; therefore, effective separation of the HOMO orbit from the LUMO is achieved, the exciton quenching caused by π-π stacking is weakened, and moreover, the molecule maintains a certain degree of molecular rigidity so that a higher photoluminescence quantum yield (PLQY) can be achieved, thereby obtaining a more satisfactory device performance.

The doping devices with P1-P6, P21 and P30 as dopant light emitting materials and mCBP as the host material achieve the maximum external quantum efficiency of 14.5%, which is further improved as compared with non-doping devices. It indicates that doping can better avoid the π-π stacking effect and reduce the concentration quenching phenomenon. Using Compound P30 as a host material, a fluorescent material or phosphorescent material as a dopant, doping devices N17 to N18 are designed with the structure: ITO (100 nm)/α-NPD (40 nm)/TCTA (10 nm)/P30: the Dopant (a fluorescent material or phosphorescent material) (40 nm)/TmPyPb (50 nm)/LiF (0.5 nm)/Al (100 nm). The fluorescent material is selected from rubrene and the phosphorescent material is selected from Ir(ppy)3. The results are shown in Table 4.

It can be seen from Table 4 that the doping devices with Compound P30 of the present disclosure as a host material and rubrene and Ir(ppy)3 as dopant materials achieve the maximum external quantum efficiencies of 7.5% and 18.0%, respectively. It indicates that the compounds in the present disclosure can be used as a host material for a fluorescent material and a phosphorescent material.

TABLE 4

Property results of doping devices prepared by vacuum vapor deposition

| Device | $V_{on}$ [V] | $CE_{(10\ mA/cm^2)}$ (cd A$^{-1}$) | $EQE_{(max)}$ (%) |
|---|---|---|---|
| N17 | 5.25 | 11.3 | 7.5 |
| N18 | 2.35 | 38 | 18.0 |

Devices Prepared through Solution Method

Moreover, we also process and fabricate the corresponding doping device N19 and non-doping device N20 by using the solution method. The structures of the devices are as follows.

The structure of the doping device is: ITO (100 nm)/PEDOT:PSS (40 nm)/PVK: P3(40 nm)/TmPyPb(50 nm)/LiF (0.5 nm)/Al (100 nm). The doping device uses the classic polymer material PVK as the host material.

The structure of the non-doping device is: ITO (100 nm)/PEDOT:PSS (40 nm)/P3 (40 nm)/TmPyPb(50 nm)/LiF (0.5 nm)/Al(100 nm).

The relevant data of the above devices are shown in Table 5.

As can be seen from Table 5, the non-doping and doping devices prepared by the solution method using the compound of the present disclosure as a light emitting material achieve the maximum external quantum efficiencies of 8.7% and 11.4%, respectively. It indicates that due to the introduction of the thiophene group, the interaction between the D unit and the A unit in the molecule becomes stronger, and the molecular twisting strength increases, and a large dihedral angle is formed; therefore, effective separation of the HOMO orbit from the LUMO is achieved, the exciton quenching caused by π-π E stacking is weakened, and moreover, the molecule maintains a certain degree of molecular rigidity so that a higher photoluminescence quantum yield (PLQY) can be achieved, thereby obtaining a more satisfactory device performance. Furthermore, the doping device is improved further in comparison with the non-doping device. It indicates that doping can better avoid the π-π stacking effect and reduce the concentration quenching phenomenon.

TABLE 5

Property results of devices prepared through solution method

| Device | $V_{on}$ [V] | $CE_{(10\ mA/cm^2)}$ (cd A$^{-1}$) | $EQE_{(max)}$ (%) |
|---|---|---|---|
| N19 | 4.8 | 14.5 | 11.4 |
| N20 | 4.6 | 10.2 | 8.7 |

Therefore, provided that these modifications and variations of the present disclosure fall within the scope of the claims of the present disclosure and their equivalent technologies, the present disclosure is also intended to include these modifications and variations.

The invention claimed is:

1. A compound, having a structure shown as formula (I):

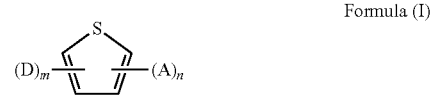

Formula (I)

wherein D represents an electron donor unit, A represents an electron acceptor unit, m and n are each independently selected from 1, 2 or 3, and m+n≤4;

wherein the A unit is selected from one or more of a triaryl boron substituent, a benzophenone substituent, an aromatic heterocyclic ketone substituent, and a sulfone substituent;

wherein the D unit is selected based on any one of following schemes:

scheme 1: the D unit is selected from any one or more of the following structures:

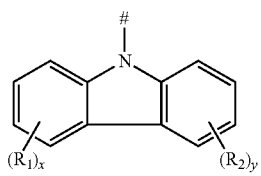
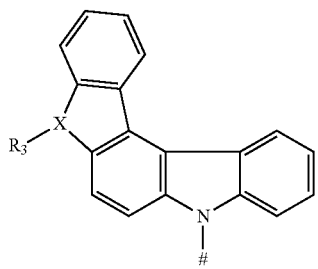
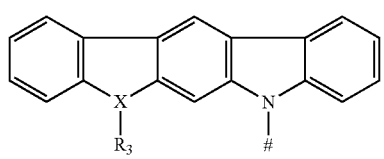
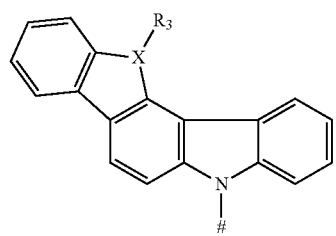
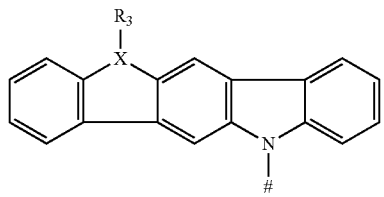
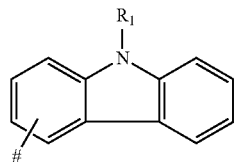
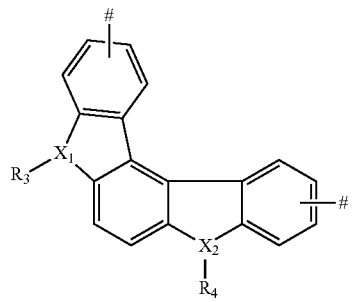
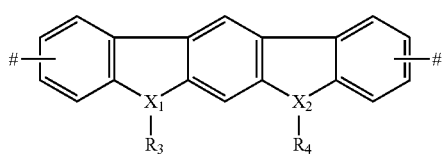

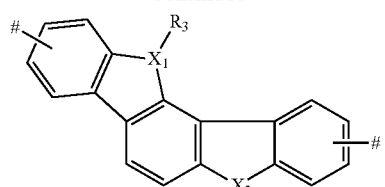
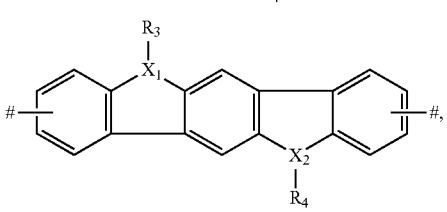

wherein X, $X_1$ and $X_2$ are each independently selected from, a nitrogen atom, an oxygen atom, or a sulfur atom;

# represents a position which can be linked to

;

x and y are each independently selected from 0, 1, 2 or 3;

$R_1$, $R_2$, $R_3$, and $R_4$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups;

when X is an oxygen atom or a sulfur atom, $R_3$ is not present; when $X_1$ is an oxygen atom or a sulfur atom, $R_3$ is not present; when $X_2$ is an oxygen atom or a sulfur atom, $R_4$ is not present;

or scheme 2: the D unit is selected from any one or more of the following structures:

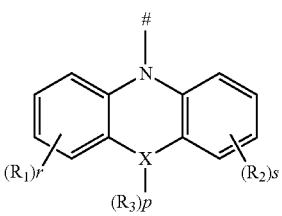

-continued

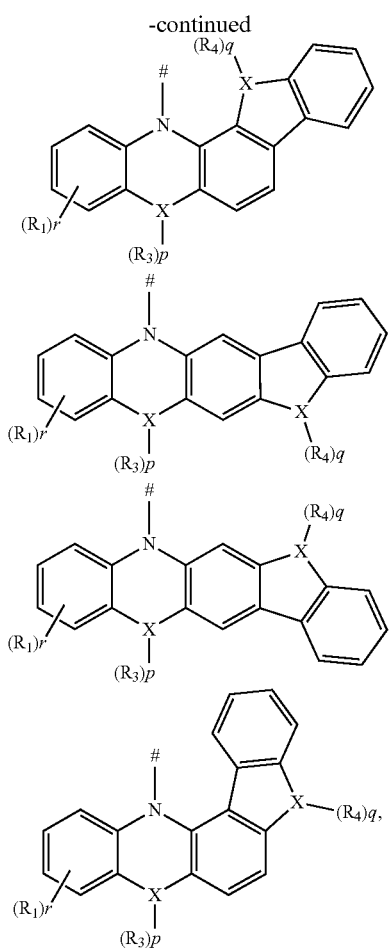

wherein X is selected from a carbon atom, a nitrogen atom, an oxygen atom, a sulfur atom or a silicon atom;
# represents a position which is linked to

r and s are each independently selected from 0, 1, 2 or 3, p and q are each independently selected from 0, 1 or 2; $R_1$, $R_2$, $R_3$, and $R_4$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups;
when X represents an oxygen atom or a sulfur atom, p=0 and q=0; when X represents a nitrogen atom, p=1 and q=1; when X represents a carbon atom or a silicon atom, p=2 and q=2;

or,
scheme 3: the D unit is selected from any one or more of the following structures:

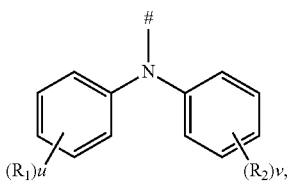

# represents a position which is linked to

u and v are each independently selected from 0, 1, 2 or 3; $R_1$ and $R_2$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups;
or,
scheme 4: the D unit is selected from any one or more of the following structures:

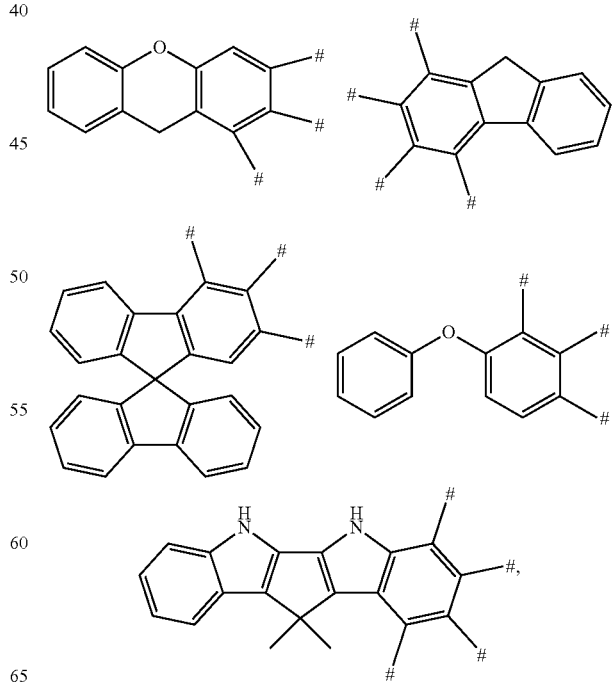

wherein # represents a position which can be linked to
2. The compound according to claim 1, wherein in the compound, at least one D unit and at least one A unit are respectively linked to an adjacent —CH— on a
ring.
3. The compound according to claim 1, wherein when the D unit is selected based on the scheme 1, the D unit is selected from any one or more of the following structures:
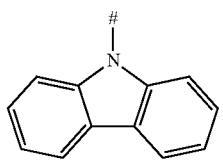 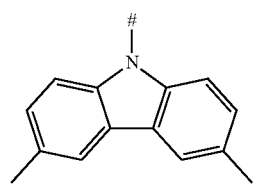
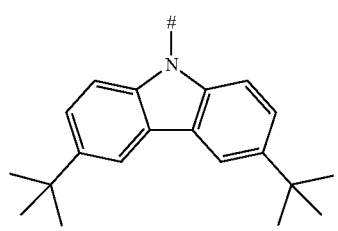
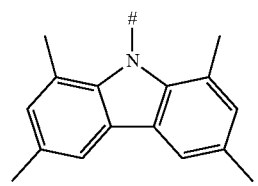
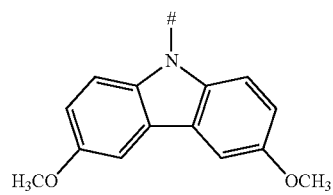
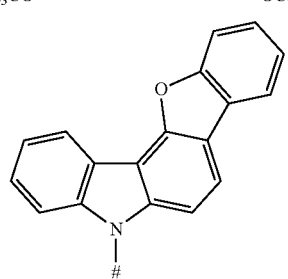
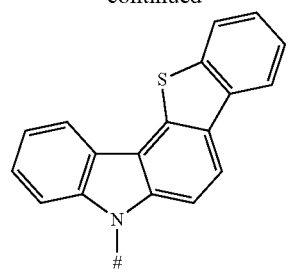
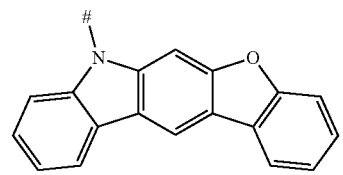
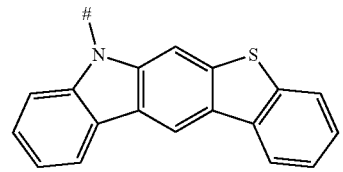
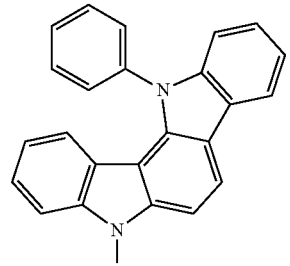
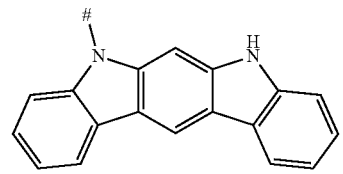
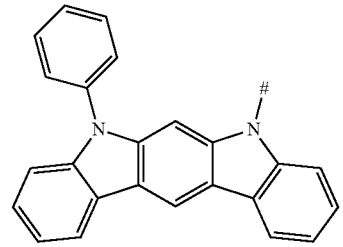
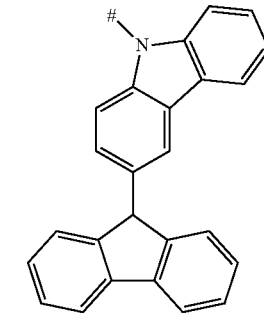

71
-continued

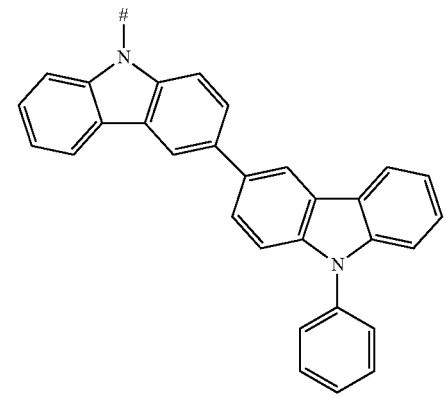

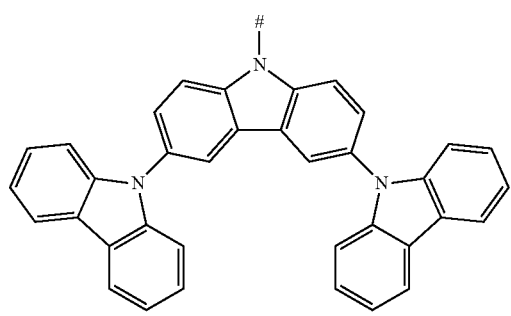

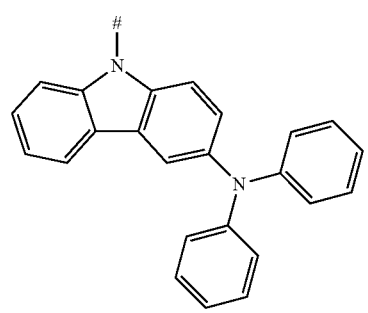

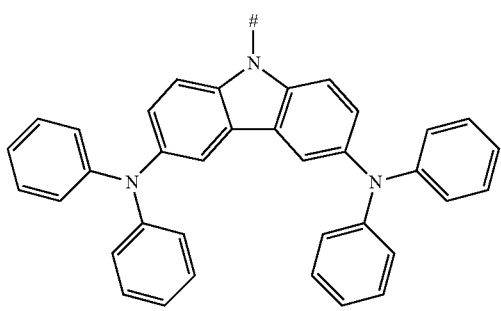

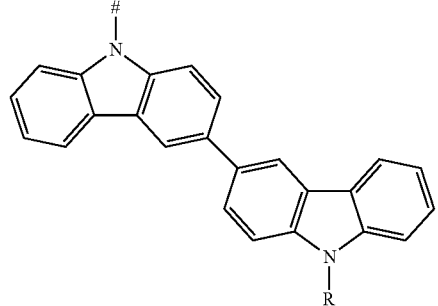

72
-continued

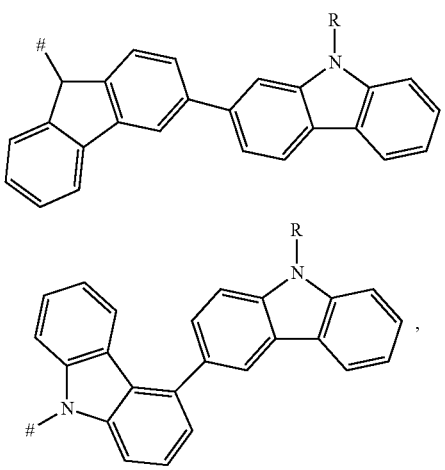

wherein # represents a position which is linked to

R in each structural formula independently represents an alkyl group having 1 to 20 carbon atoms, an alkoxy group having 1 to 20 carbon atoms, an alkenyl group having 2 to 20 carbon atoms, an alkynyl group having 2 to 20 carbon atoms, an aromatic group having 6 to 40 carbon atoms, and a heteromatic group having 4 to 40 carbon atoms.

4. The compound according to claim 1, wherein when the D unit is selected based on the scheme 2, the D unit is selected from any one or more of the following structures:

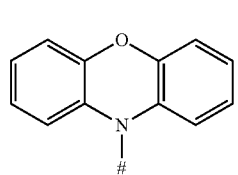 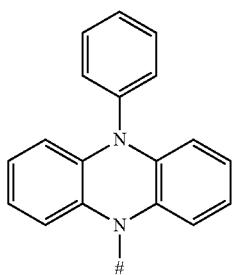

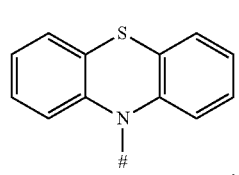 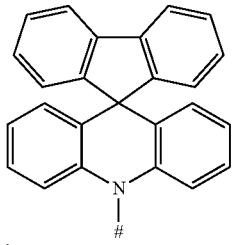

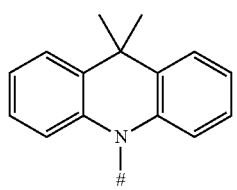

-continued
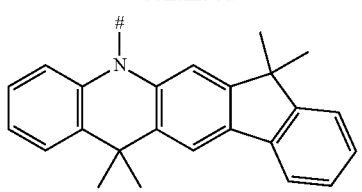
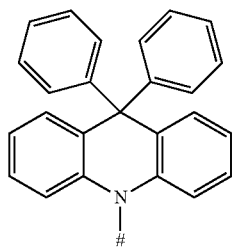
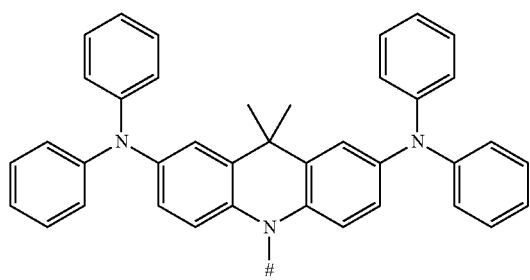
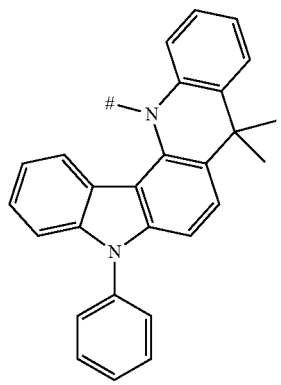
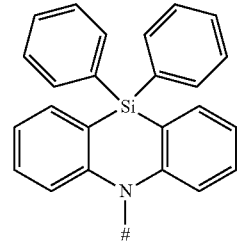
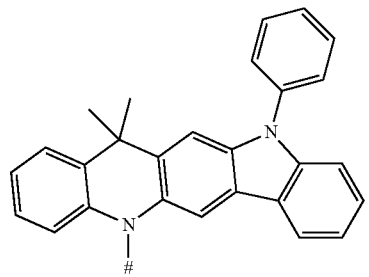
-continued
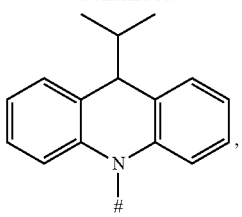
wherein # represents a position which is linked to
.
5. The compound according to claim 1, wherein when the D unit is selected based on the scheme 3, the D unit is selected from any one or more of the following structures:
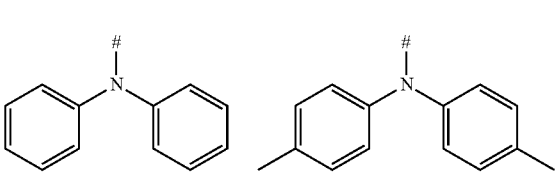
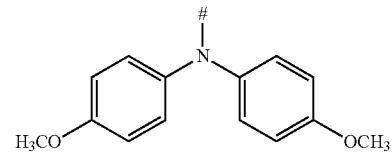
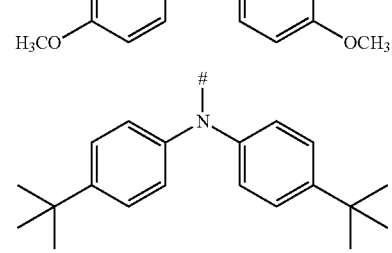
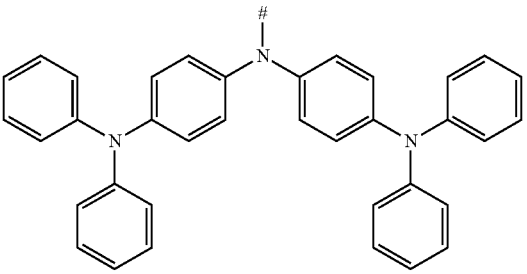
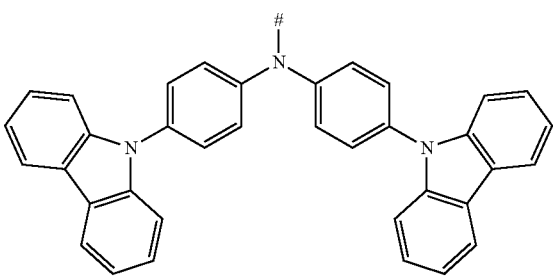

75
-continued
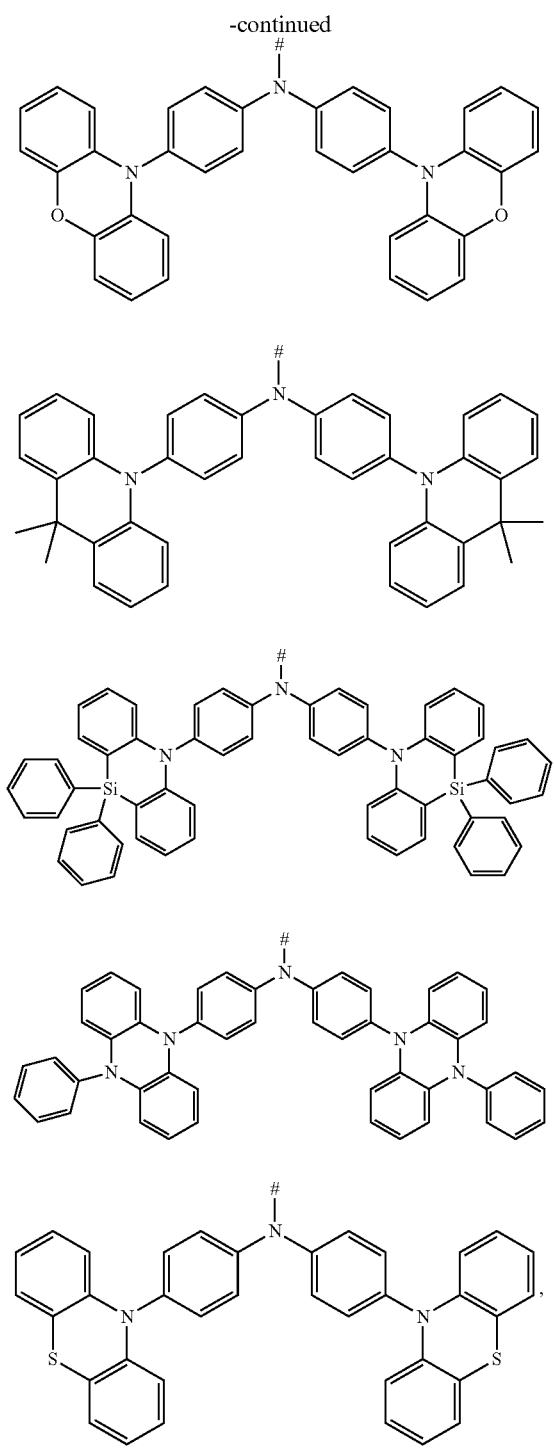
wherein # indicates a position which is linked to
6. The compound according to claim 1, wherein the triaryl boron substituent is selected from one or more of the following structures:
76
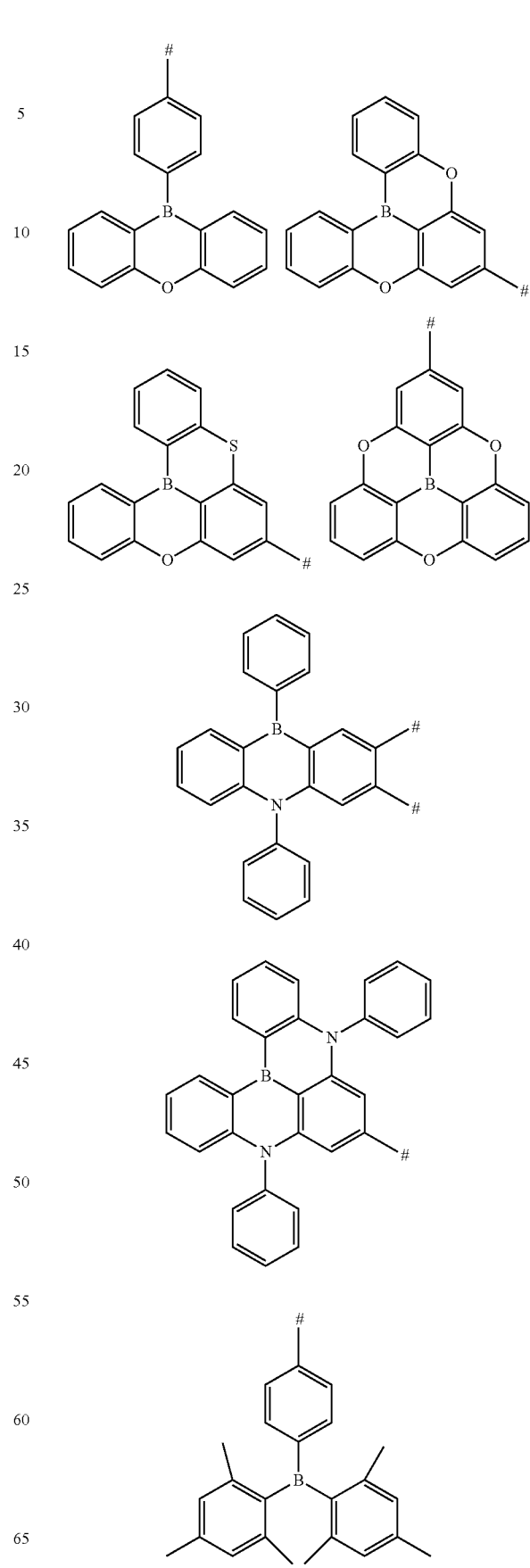

-continued

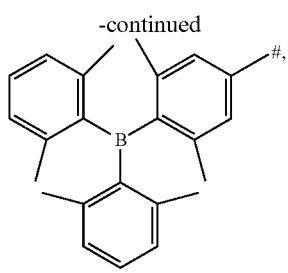

wherein # represents a position which can be linked to

7. The compound according to claim 1, wherein the aromatic heterocyclic ketone substituent is selected from one or more of the following structures:

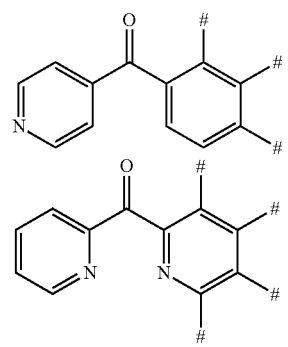

and the benzophenone substituent selected from one or more of the following structures:
wherein # represents a position which can be linked to

R in each structural formula independently represents an alkyl group having 1 to 20 carbon atoms, an alkoxy group having 1 to 20 carbon atoms, an alkenyl group having 2 to 20 carbon atoms, an alkynyl group having 2 to 20 carbon atoms, a naphthenic group having 4 to 8 carbon atoms, an aromatic group having 6 to 40 carbon atoms, or a heteromatic group having 4 to 40 carbon atoms.

8. The compound according to claim 1, wherein the sulfone substituent is selected from one or more of the following structures:
wherein # represents a position which can be linked to

9. The compound according to claim 1, wherein the compound is selected from one of following compounds:

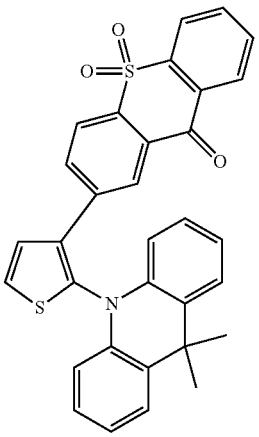

P2

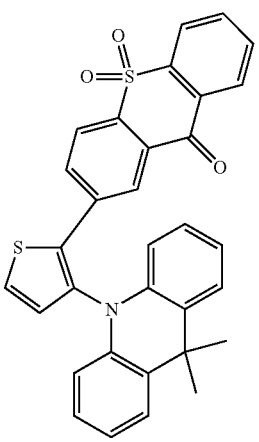

P3

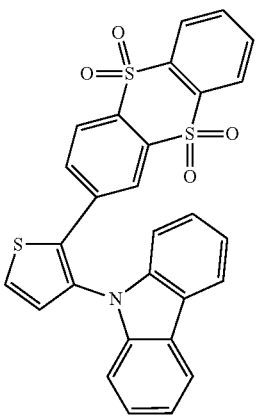

P4

P14
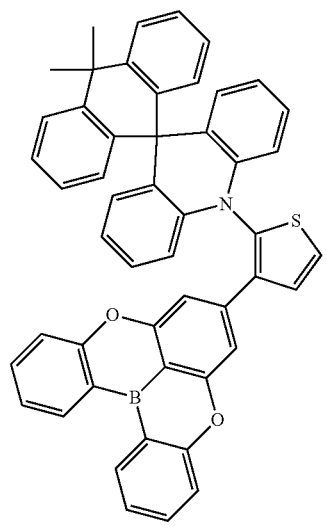
P17
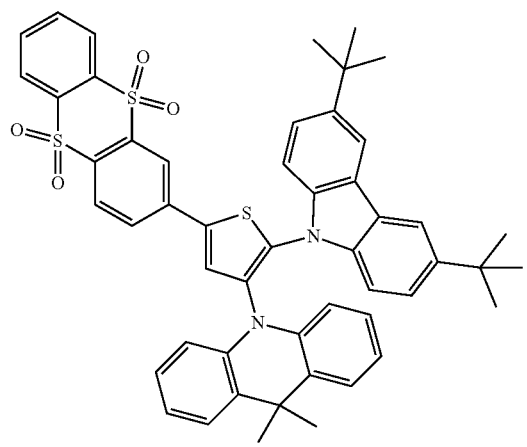
P18
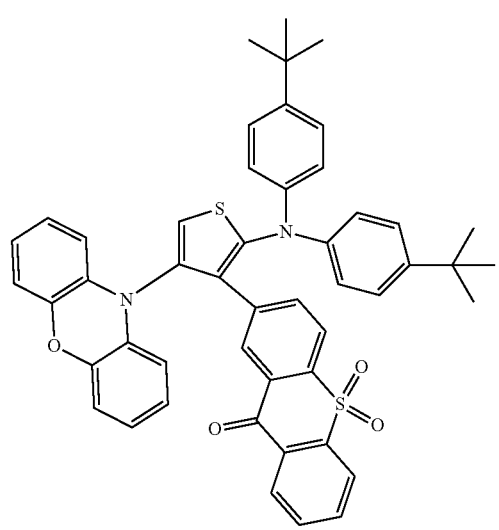
P20
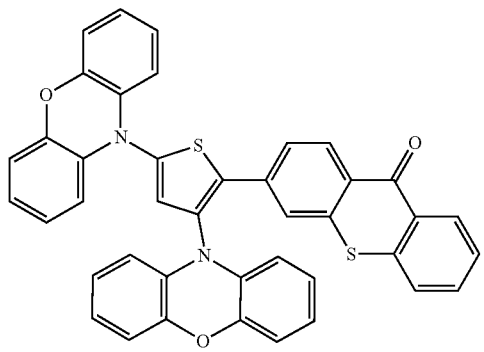
P21
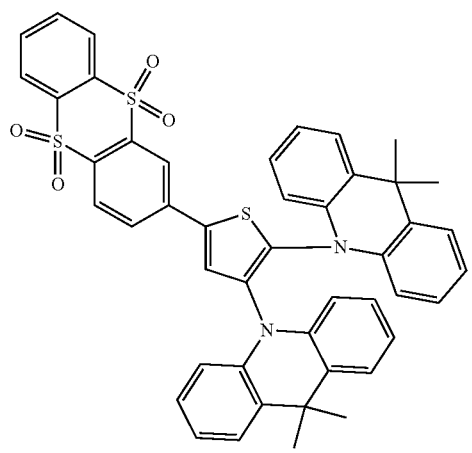
P23
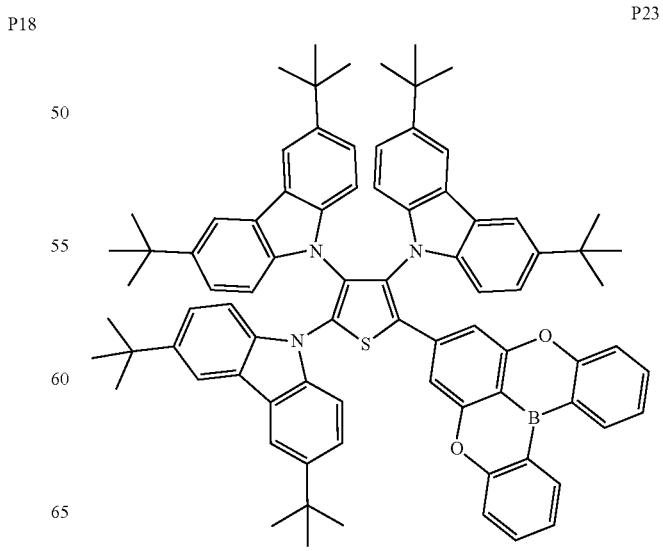

P25

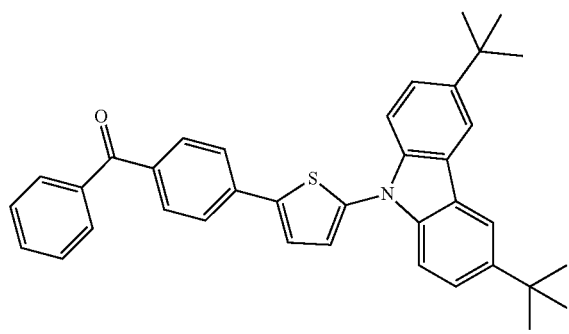

P26

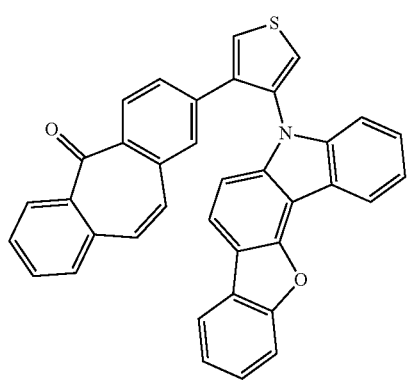

P27

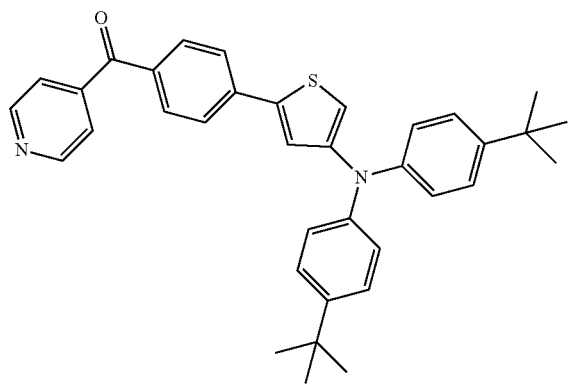

P28

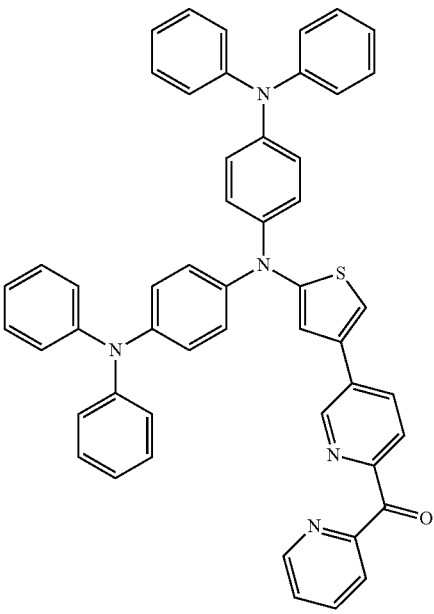

P29

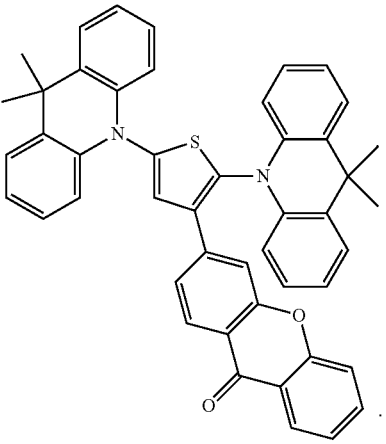

10. The compound according to claim 1, wherein the difference between the singlet energy and the triplet energy of the compound is less than 0.3 eV.

11. An organic light emitting display device, comprising an organic electroluminescent device, the organic electroluminescent device comprising:
an organic functional layer comprising one or more organic film layers, and at least one of the organic film layers is a light emitting layer;
the light emitting layer comprises a light emitting material, and the light emitting material comprises the compound of claim 1.

12. The organic light emitting display device according to claim 11, wherein the compound functions as a host material or a guest material of the light emitting layer, or the compound constitutes the light emitting layer alone to prepare a non-doping organic light emitting display device.

13. The organic light emitting display device according to claim 11, wherein the compound functions as a red light emitting material of the light emitting layer, and the singlet energy of the red light emitting material is located between 1.61 eV and 1.99 eV.

14. The organic light emitting display device according to claim 11, wherein the compound functions as a green light emitting material of the light emitting layer, and the singlet energy of the green light emitting material is located between 2.15 eV and 2.52 eV.

15. The organic light emitting display device according to claim 11, wherein the compound functions as a blue light emitting material of the light emitting layer, and the singlet energy of the blue light emitting material is located between 2.52 eV and 2.73 eV.

16. The organic light emitting display device according to claim 11, wherein the compound functions as a guest material of a light emitting material, and a host material is any one or more of 2,8-bis(diphenylphosphinyloxy)dibenzothiophene,
    4,4'-di(9-carbazolyl) biphenyl, 3,3'-bis(N-carbazolyl)-1,1'-biphenyl,
    2,8-bis(diphenylphosphinyloxy)bis benzofuran,
    bis(4-(9H-carbazolyl-9-yl)phenyl)diphenylsilane,
    9-(4-t-butylphenyl)-3,6-bis(triphenylsilyl)-9h-carbazole,
    bis(2-diphenylphosphine oxide)diphenyl ether, 1,3-bis[3,5-bis(pyridin-3-yl)phenyl]benzene,
    4,6-bis(3,5-bis(3-pyridyl)phenyl)-2-methylpyrimidine,
    9-(3-(9H-carbazolyl)-9-yl)phenyl)-9H-carbazole-3-cyano,
    9-phenyl-9-[4-(triphenylsilyl)phenyl]-9H-fluorene,
    1,3,5-tris(1-phenyl-1H-benzimidazol-2-yl)benzene,
    diphenyl[4-(triphenylsilyl)phenyl]phosphine oxide,
    4,4',4"-tris(carbazolyl-9-yl)triphenylamine, 2,6-dicarbazole-1,5-pyridine, polyvinylcarbazole and polyfluorene; the difference between the Highest Occupied Molecular Orbital (HOMO) of the host material and the HOMO of the guest material is less than 0.6 eV, or the difference between the Lowest Unoccupied Molecular Orbital (LUMO) of the host material and the LUMO of the guest material is less than 0.6 eV.

17. The organic light emitting display device according to claim 16, wherein the singlet energy of the host material is higher than the singlet energy of the guest material, and the difference between the singlet energy of the host material and the singlet energy of the guest material is less than 1.0 eV.

18. The organic light emitting display device according to claim 11, wherein the compound functions as a host material of a light emitting material, and a guest material is selected from a fluorescent material, a thermally activated delayed fluorescence (TADF) material, or a phosphorescent light emitting material, and the difference between the HOMO of the host material and the HOMO of the guest material is less than 0.6 eV, or the difference between the LUMO of the host material and the LUMO of the guest material is less than 0.6 eV.

19. The organic light emitting display device according to claim 18, wherein the compound functions as a host material of a light emitting material, and a guest material is selected from a fluorescent material or a TADF material; the singlet energy of the guest material is less than the singlet energy of the host material, and the difference between the singlet energy of the host material and the singlet energy of the guest material is less than 1.0 eV.

20. The organic light emitting display device according to claim 18, wherein the compound functions as a host material of a light emitting material, and a guest material is selected from a fluorescent material; the triplet energy of the guest material is less than the triplet energy of the host material, and the difference between the triplet energy of the host material and the triplet energy of the guest material is less than 1.0 eV.

21. The organic light emitting display device according to claim 11, wherein the light emitting material is a TADF material.

22. A compound, having a structure shown as formula (I):

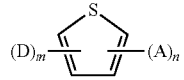

Formula (I)

wherein D represents an electron donor unit, A represents an electron acceptor unit, m and n are each independently selected from 1, 2 or 3, and m+n≤4;

wherein the D unit is selected from any one or more of the following structures:

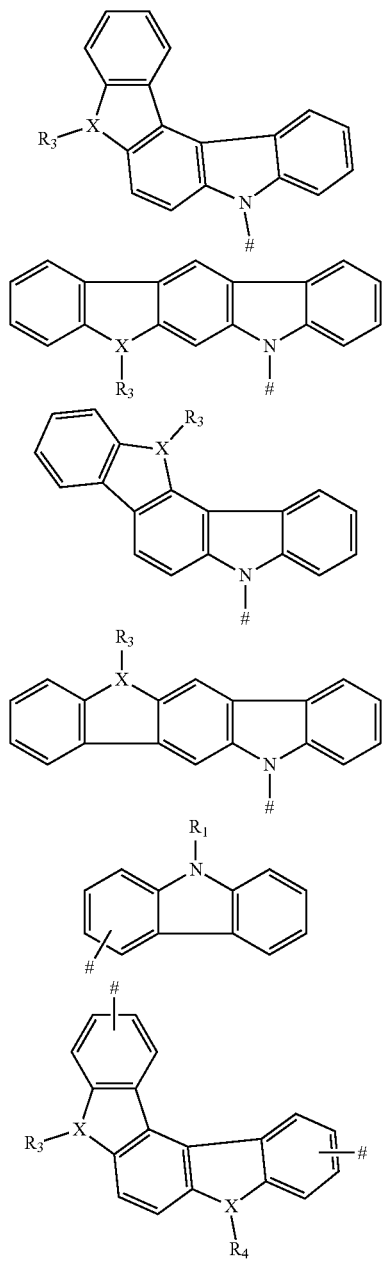

-continued

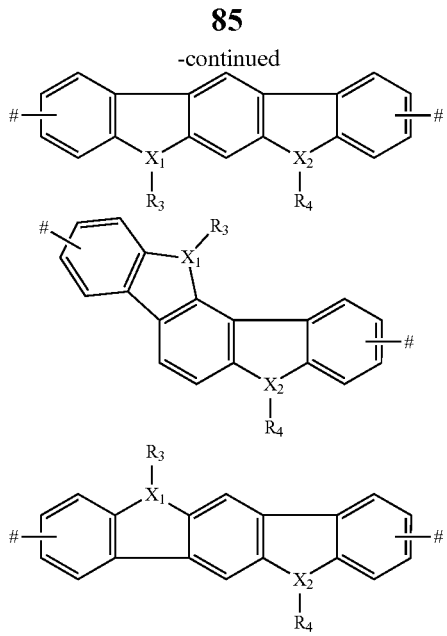

wherein X, $X_1$ and $X_2$ are each independently selected from, a nitrogen atom, an oxygen atom, or a sulfur atom;

# represents a position which can be linked to

$R_1$, $R_2$, $R_3$, and $R_4$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups;

when X is an oxygen atom or a sulfur atom, $R_3$ is not present; when $X_1$ is an oxygen atom or a sulfur atom, $R_3$ is not present; when $X_2$ is an oxygen atom or a sulfur atom, $R_4$ is not present;

or wherein the D unit is selected from any one or more of the following structures:

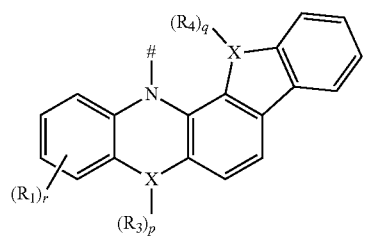

-continued

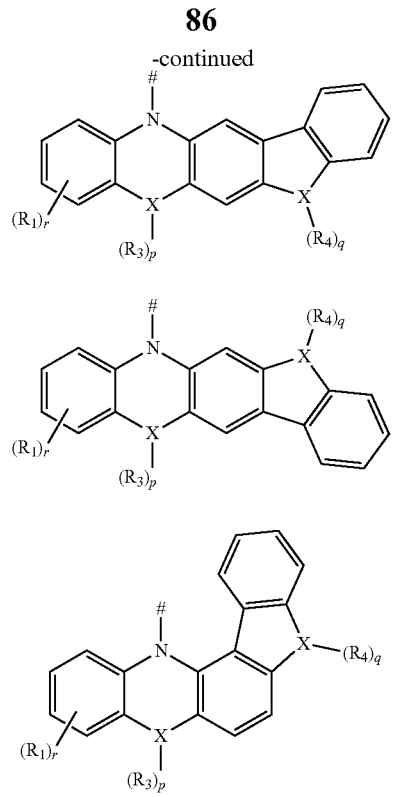

wherein X is selected from a carbon atom, a nitrogen atom, an oxygen atom, a sulfur atom or a silicon atom;

# represents a position which is linked to

r is selected from 0, 1, 2 or 3, p and q are each independently selected from 0, 1 or 2;

$R_1$, $R_2$, $R_3$, and $R_4$ are each independently selected from any one or more of a hydrogen atom, an alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 4 to 40 carbon atoms, a substituted or unsubstituted carbazolyl group having 12 to 40 carbon atoms and its derivative groups, a substituted or unsubstituted diphenylamino group having 12 to 40 carbon atoms and its derivative groups, a substituted or unsubstituted acridinyl group having 12 to 40 carbon atoms and its derivative groups, and a substituted or unsubstituted azine group having 3 to 40 carbon atoms and its derivative groups;

when X represents an oxygen atom or a sulfur atom, p=0 and q=0; when X represents a nitrogen atom, p=1 and q=1; when X represents a carbon atom or a silicon atom, p=2 and q=2;

or wherein the D unit is selected from any one or more of the following structures:

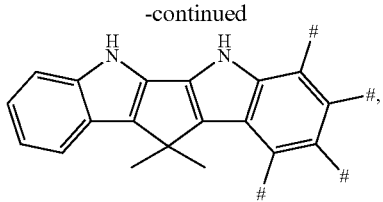
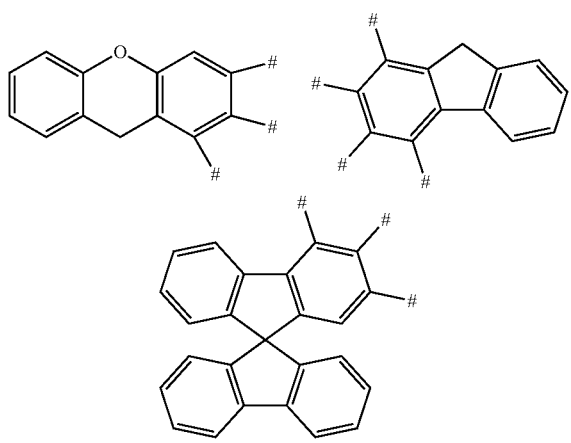
wherein # represents a position which can be linked to
* * * * *